US009867835B2

(12) United States Patent
Zasloff

(10) Patent No.: US 9,867,835 B2
(45) Date of Patent: Jan. 16, 2018

(54) METHODS AND COMPOSITIONS FOR TREATING AND PREVENTING VIRAL INFECTIONS

(71) Applicant: ENTERIN LABORATORIES, INC., Merion, PA (US)

(72) Inventor: Michael Zasloff, Merion, PA (US)

(73) Assignee: ENTERIN LABORATORIES, INC., Merion, PA (US)

( * ) Notice: Subject to any disclaimer, the term of this patent is extended or adjusted under 35 U.S.C. 154(b) by 0 days.

(21) Appl. No.: 14/274,236

(22) Filed: May 9, 2014

(65) Prior Publication Data

US 2014/0328792 A1 Nov. 6, 2014

Related U.S. Application Data

(62) Division of application No. 12/913,648, filed on Oct. 27, 2010, now Pat. No. 8,729,058.

(60) Provisional application No. 61/255,394, filed on Oct. 27, 2009.

(51) Int. Cl.
*A61K 31/575* (2006.01)
*A61K 31/56* (2006.01)
*A61K 45/06* (2006.01)
*A61K 38/21* (2006.01)

(52) U.S. Cl.
CPC ............ *A61K 31/575* (2013.01); *A61K 31/56* (2013.01); *A61K 38/212* (2013.01); *A61K 45/06* (2013.01)

(58) Field of Classification Search
USPC ................................................. 514/171, 182
See application file for complete search history.

(56) References Cited

U.S. PATENT DOCUMENTS

| | | | |
|---|---|---|---|
| 3,773,919 A | 11/1973 | Boswell et al. |
| 4,485,045 A | 11/1984 | Regen |
| 4,544,545 A | 10/1985 | Ryan et al. |
| 5,021,234 A | 6/1991 | Ehrenfeld |
| 5,192,756 A | 3/1993 | Zasloff et al. |
| 5,637,691 A | 6/1997 | Frye et al. |
| 5,721,226 A | 2/1998 | Frye et al. |
| 5,733,899 A | 3/1998 | Frye et al. |
| 5,763,430 A | 6/1998 | Zasloff |
| 5,792,635 A | 8/1998 | Zasloff |

(Continued)

FOREIGN PATENT DOCUMENTS

| | | |
|---|---|---|
| EP | 0 102 324 A2 | 3/1984 |
| EP | 0 052 322 B1 | 3/1985 |

(Continued)

OTHER PUBLICATIONS

Notification of Transmittal of the International Search Report and the Written Opinion cited in related International Patent Application No. PCT/US2010/054285, dated Jul. 12, 2011.

(Continued)

*Primary Examiner* — San-Ming Hui
(74) *Attorney, Agent, or Firm* — Foley & Lardner LLP

(57) ABSTRACT

A method of treating or preventing a systemic viral infection in a mammal by administering a pharmaceutically acceptable composition selected from the group consisting of squalamine, an active isomer thereof, and an active analogue thereof, via a dosing regimen that delivers effective antiviral concentrations of squalamine. Also compositions for achieving the systemic antiviral effect.

20 Claims, 10 Drawing Sheets

(56) References Cited

U.S. PATENT DOCUMENTS

| | | |
|---|---|---|
| 5,795,885 A | 8/1998 | Zasloff et al. |
| 5,834,453 A | 11/1998 | Regen |
| 5,840,740 A | 11/1998 | Zasloff et al. |
| 5,840,936 A | 11/1998 | Zasloff et al. |
| 5,847,172 A | 12/1998 | Zasloff et al. |
| 5,856,535 A | 1/1999 | Zasloff et al. |
| 5,874,597 A | 2/1999 | Jones |
| 5,994,336 A | 11/1999 | Zasloff et al. |
| 6,017,906 A | 1/2000 | Mintz et al. |
| 6,143,738 A | 11/2000 | Zasloff |
| 6,147,060 A | 11/2000 | Zasloff et al. |
| 6,388,108 B1 | 5/2002 | Rao et al. |
| 6,488,936 B1 * | 12/2002 | Mishkin ............ A61K 39/245 424/204.1 |
| 6,596,712 B2 | 7/2003 | Zasloff et al. |
| 6,962,909 B2 | 11/2005 | Zasloff et al. |
| 7,981,876 B2 * | 7/2011 | Chellquist ............ C07J 41/0005 514/182 |
| 2005/0261508 A1 | 11/2005 | Zasloff et al. |
| 2006/0166950 A1 | 7/2006 | Zasloff et al. |
| 2006/0183928 A1 | 8/2006 | Zasloff et al. |
| 2007/0010504 A1 | 1/2007 | Chellquist et al. |

FOREIGN PATENT DOCUMENTS

| | | |
|---|---|---|
| EP | 0 058 481 B2 | 10/1986 |
| EP | 0 088 046 B1 | 12/1987 |
| EP | 0 143 949 B1 | 10/1988 |
| EP | 0 036 676 B2 | 9/1990 |
| EP | 0 142 641 B1 | 1/1991 |
| WO | WO 96/08270 A2 | 3/1996 |
| WO | WO 98/17281 | 4/1998 |
| WO | WO 98/30213 | 7/1998 |
| WO | WO 98/50347 | 11/1998 |
| WO | WO 99/49830 | 10/1999 |
| WO | WO 99/56764 | 11/1999 |
| WO | WO 99/66936 | 12/1999 |

OTHER PUBLICATIONS

International Preliminary Report on Patentability issued in related International Patent Application No. PCT/US2010/054285, dated May 10, 2012.

English Abstract of Mertz et al., JAMA, vol. 260, No. 2, pp. 201-206 (1988).

\* cited by examiner

FIGURE 1
Figure 1A
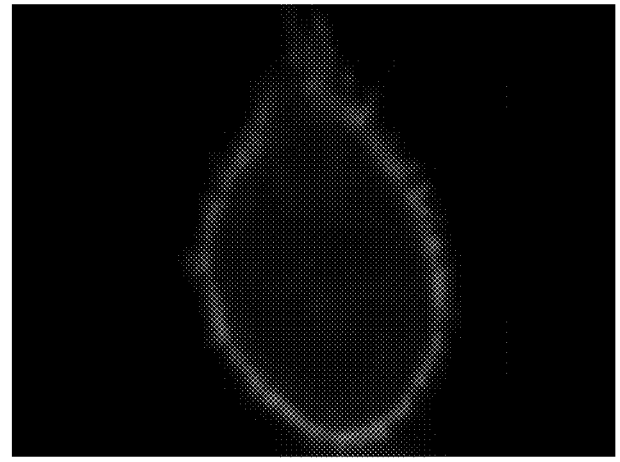
Figure 1B
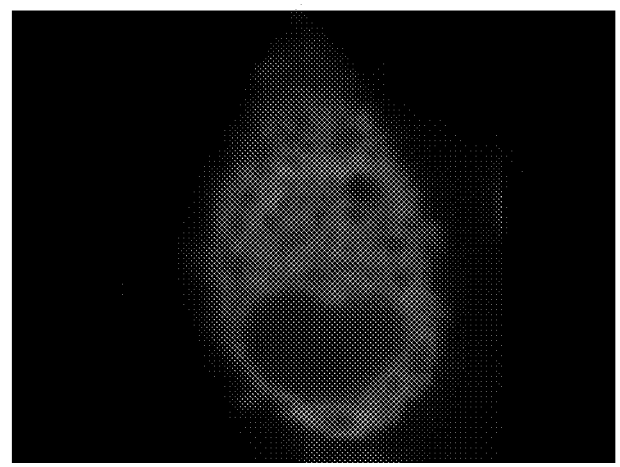

FIGURE 3
Figure 3A
Figure 3B
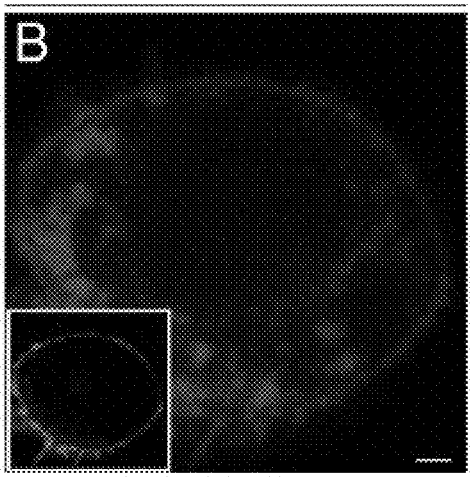
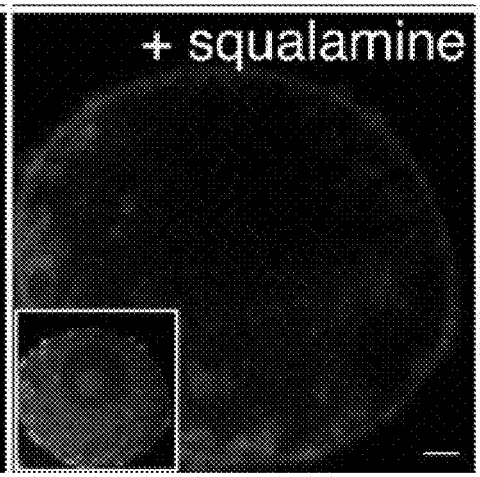

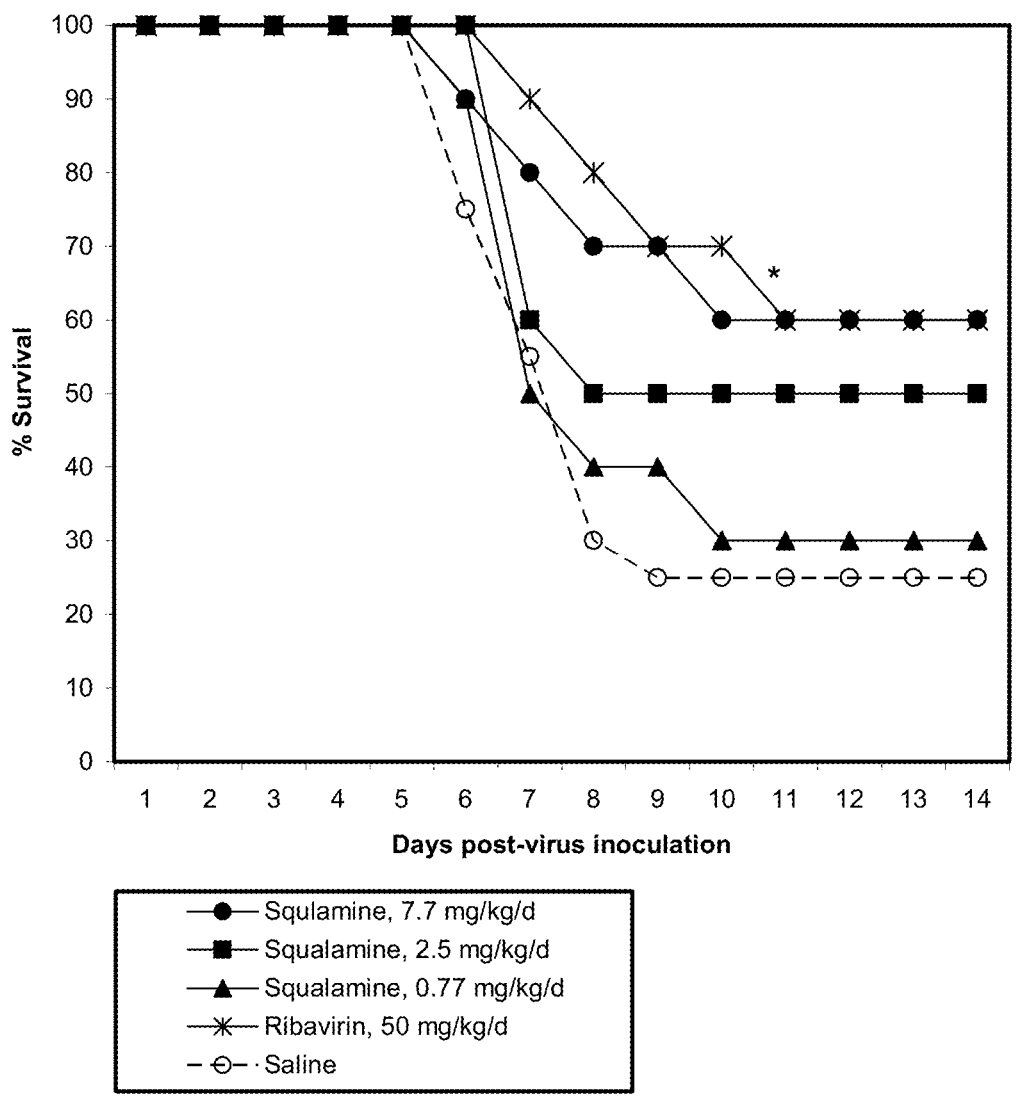

FIGURE 8

Survival of Golden Syrian hamsters (Charles River) infected SC with eastern equine encephalitis virus (EEEV) and treated with squalamine (10 mg/kg/day SC)

Logrank Test: p=0.0566

FIGURE 9

Viremia of Golden Syrian hamsters (Charles River) infected SC with eastern equine encephalitis virus (EEEV) and treated with squalamine (10 mg/kg/day SC)

*In vitro* antiviral activity of squalamine against Dengue, as studied in a human endothelial cell line

METHODS AND COMPOSITIONS FOR TREATING AND PREVENTING VIRAL INFECTIONS

CROSS-REFERENCE TO RELATED APPLICATIONS

This application is a divisional of U.S. patent application Ser. No. 12/913,648, filed Oct. 27, 2010, now U.S. Pat. No. 8,729,058, which claims priority of U.S. Provisional Patent Application No. 61/255,394, filed on Oct. 27, 2009. The contents of these applications are incorporated herein by reference in their entirety.

FIELD OF THE INVENTION

This invention relates to methods of preventing and/or treating human and animal viral infections. The method comprises administering squalamine or a derivative thereof to a subject in need, which results in altering the lipid composition of the membranes of the tissues of the treated subject to create a state refractory to viral infection.

BACKGROUND OF THE INVENTION

A. Background Regarding Squalamine

Chemically squalamine presented a structure never before seen in nature that being a bile acid coupled to a polyamine (spermidine):

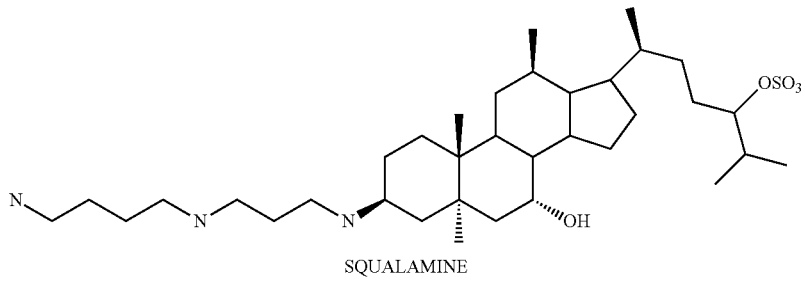

SQUALAMINE

The discovery of squalamine, the structure of which is shown above, was reported by Michael Zasloff in 1993 (U.S. Pat. No. 5,192,756). Squalamine was discovered in various tissues of the dogfish shark (*Squalus acanthias*) in a search for antibacterial agents. The most abundant source of squalamine is in the livers of *Squalus acanthias*, though it is found in other sources, such as lampreys (Yun et al., "Identification of Squalamine in the Plasma Membrane of White Blood Cells in the Sea Lamprey," *Petromyzon marinus*," *J. Lipid Res.*, 48(12): 2579-2586 (2007)).

Numerous studies later demonstrated that squalamine exhibits potent antibacterial activity in vitro (Salmi, Loncle et al. 2008). Subsequently, squalamine was discovered to exhibit antiangiogenic activity in vitro and upon administration to animals (Sills, Williams et al. 1998; Yin, Gentili et al. 2002). As a consequence, squalamine has been evaluated in disease states known to be associated with pathological neovascularization, such as cancer (Sills, Williams et al. 1998; Schiller and Bittner 1999; Bhargava, Marshall et al. 2001; Williams, Weitman et al. 2001; Hao, Hammond et al. 2003; Herbst, Hammond et al. 2003; Sokoloff, Rinker-Schaeffer et al. 2004), and vascular disorders of the eye, including macular degeneration (US2007/10504A1 2007), retinopathy of prematurity (Higgins, Sanders et al. 2000; Higgins, Yan et al. 2004; US2007/10504A1 2007), corneal neovascularization (Genaidy, Kazi et al. 2002) and diabetic retinopathy (US2007/10504A1 2007).

The utility of squalamine as an anti-infective has been demonstrated in vitro against bacteria and fungi (Moore, Wehrli et al. 1993; Rao, Shinnar et al. 2000; Salmi, Loncle et al. 2008). Squalamine is a cationic amphipathic substance exhibiting an affinity for membranes composed of anionic phospholipids (Selinsky, Zhou et al. 1998; Selinsky, Smith et al. 2000). Like other such agents, including magainin and cationic antimicrobial peptides, squalamine is believed to exert antimicrobial action by interacting electrostatically with the membranes of target microorganisms, which generally display anionic phospholipids on the membrane surface exposed to the environment, subsequently disturbing their functional integrity, and causing death of the targeted microbe (Sills, Williams et al. 1998; Zasloff 2002; Salmi, Loncle et al. 2008).

To date, squalamine has not been reported to display efficacy as an anti-infective in a living animal. In no published patent application or issued patent has such evidence been reported (U.S. Pat. Nos. 5,192,756; 5,637,691; 5,721,226; 5,733,899; 5,763,430; 5,792,635; 5,795,885; 5,840,740; 5,840,936; 5,847,172; 5,856,535; 5,874,597; 5,994,336; 6,017,906; 6,143,738; 6,147,060; 6,388,108; 6,596,712; U.S. Patent Publication No. 2005/0261508A1 2005; U.S. Pat. No. 6,962,909; U.S. Patent Publication No. 2006/0166950A1 2006; U.S. Patent Publication No. 2006/0183928A1 2006; U.S. Patent Publication No. 2007/10504A1 2007-).

Recent studies have revealed that squalamine is inactivated by the concentrations of ionized calcium and magnesium present in mammalian blood, preventing squalamine from exerting its antimicrobial activity in the setting of systemic bacterial, fungal, or protozoan infections (Salmi, Loncle et al. 2008).

Most studies of mechanism of squalamine have focused on the effects of squalamine on properties of the endothelial cell. The compound has been shown to inhibit many downstream effects stimulated by diverse growth-factors (VEGF, thrombin, FGF) including cellular proliferation, cellular migration, vascular tube formation, sodium-proton antiporter activation. (Sills et al., "Squalamine inhibits angiogenesis and solid tumor growth in vivo and perturbs embryonic vasculature," Cancer Res 58, 2784-92 (1998); Li et al., "Squalamine and cisplatin block angiogenesis and growth of human ovarian cancer cells with or without HER-2 gene overexpression," Oncogene 21, 2805-14 (2002); Akhter et al., "Squalamine, a novel cationic steroid, specifically inhibits the brush-border Na+/H+ exchanger isoform NHE3," Am J Physiol 276, C136-44 (1999); and Williams et al., "Squalamine treatment of human tumors in nu/nu mice enhances platinum-based chemotherapies," Clin Cancer Res 7, 724-33 (2001)).

No mention of squalamine's use as a systemic antimicrobial agent, for example, appears in a recent patent application (U.S. Patent Publication No. 2007/10504A1), which describes a favored salt form of squalamine for therapeutic administration, and which addresses the utility of squalamine as a systemic agent in the treatment of disorders of neovascularization and cancer.

To date, no published data describe or support the efficacy of squalamine in treating or preventing a systemic viral infection in an animal. It has been reported in a patent application that squalamine could inhibit the infectivity of HIV and HSV in tissue culture (WO96/08270). However, it was not reported at that time, nor until the invention disclosed herein, that squalamine could exhibit antiviral activity when administered systemically to an animal. In the experiments described in WO96/08270, squalamine was conceived as a component of a topical agent to be used as a "chemical condom", acting as a microbicide, and capable of rapidly inactivating HIV or HSV on contact by disrupting the outermost membranous envelopes of the viruses. Thus, the antiviral properties of squalamine observed in vitro were believed to result from direct disruption of the viral membrane, via a mechanism analogous to that proposed for its antibacterial activity. The potential use of squalamine for the topical prevention of sexually transmitted diseases such as HIV, Herpes simplex, and *Neisseria gonorrhea* was presented at the 1995 ICAAC0 conference (MacDonald 1995). Thus, squalamine was proposed to have utility as an advanced form of "disinfectant," to be applied to a mucosal surface in some formulation and thereby prevent viable virus from gaining access to the epithelial surfaces of the genitourinary tract.

Squalamine has been shown to inhibit a specific isoform of the sodium-hydrogen exchanger ("NHE-3"), a protein that plays a role in numerous cellular processes that involve the control of intracellular hydrogen ions (Akhter, Nath et al. 1999). As a consequence of this activity, it was proposed that squalamine might find utility in treating diseases, including viral infections, where NHE3 played a critical role, and where its inhibition (by squalamine) could be effected (see e.g., U.S. Pat. No. 6,962,909). It has been proposed that squalamine could be used to treat viral infections should it be known that a specific virus infected a target cell expressing an NHE sensitive to inhibition (NHE-3 in the case of squalamine), and that the specific NHE played a critical role in the cellular homeostasis of that cell type, and that the virus in question naturally infected that cell type in the course of a disease process (U.S. Pat. No. 6,962,909). To date, however, no example of an NHE-3 dependent viral infection has been reported in the literature, nor has any known NHE-3 inhibitor been shown to exhibit antiviral activity in an animal, including squalamine. Furthermore the viruses demonstrated to be inactivated in vitro by squalamine, namely HIV and HSV (WO96/08270) are now known to infect cells via a pathway that is "pH independent", in the sense that inhibitors of pH homeostasis do not influence infectivity (Pelkmans and Helenius 2003).

1436 is an aminosterol, isolated from the dogfish shark, structurally related to squalamine (U.S. Pat. No. 5,840,936; Rao, Shinnar et al. 2000) Aminosterol 1436 exhibits antiviral activity against HIV in tissue culture (U.S. Pat. No. 5,763,430) via a mechanism proposed to involve inhibition of a lymphocyte-specific NHE by 1436, resulting in suppression of cytokine responsiveness, and subsequent depression of the capacity of the lymphocyte to support HIV replication (U.S. Pat. No. 5,763,430). Aminosterol 1436, however, has an additional pharmacological property, not shared with squalamine, namely potent appetite suppression and promotion of dose-dependent weigh loss (U.S. Pat. No. 6,143,738; Zasloff, Williams et al. 2001; Ahima, Patel et al. 2002). Administration of Aminosterol 1436 to animals at doses that would achieve tissue concentrations of Aminosterol 1436 speculated to exert an antiviral benefit cause profound weight loss and suppression of food intake and death due to starvation (Zasloff, Williams et al. 2001; Ahima, Patel et al. 2002).

Recent patents have been issued describing squalamine like compounds with potent antibacterial activity, but no mention is made of their utility as antiviral agents (U.S. Pat. No. 5,834,453; U.S. Pat. No. 6,017,906). Indeed, the potential value of squalamine and its analogs as systemic agents has been questioned due to the extensive binding to albumin exhibited by these compounds (U.S. Pat. No. 5,834,453).

Squalamine in its intravenous form, squalamine lactate, is in the process of being tested as a treatment of fibrodysplasia ossificans progressiva, a rare disease where connective tissue will ossify when damaged. (Genesis, A., "Squalamine trial for the treatment of fibrodysplasia ossificans progressiva initiated", *Angiogenesis Weekly*, 8:45 (2002).) Squalamine is also undergoing trials for treatment of non-small cell lung cancer (stage I/IIA) as well as general phase I pharmacokinetic studies. (Herbst et al., "A Phase I/IIA Trial of Continuous Five-Day Infusion of Squalamine Lactate (MSI-1256F) Plus Carboplatin and Paclitaxel in Patients with Advanced Non-Small Cell Lung Cancer 1", *Clinical Cancer Research*, 9:4108-4115 (2003); Hao et al., "A Phase I and Pharmacokinetic Study of Squalamine, an Aminosterol Angiogenesis Inhibitor", *Clin Cancer Res.*, 9(7): 2465-2471 (2003).) In 2005, the Food and Drug Administration granted squalamine Fast Track status for approval for treatment of age-related macular degeneration. (CATE: California Assistive Technology Exchange", California Assistive Technology Exchange, http://cate.ca.gov/index.cfm?a=Resources&p=News&article=176, Retrieved 2009-03-31.) However, Genaera Corporation discontinued trials for the use of squalamine in treating prostate cancer and wet age-related macular degeneration in 2007. ("PROSTATE CANCER; Genaera Discontinues LOMUCIN in Cystic Fibrosis and Squalamine in Prostate Cancer Studies", *Drug Week, pp.* 251. 2007-07-20; "Reports describe the most recent news from Genaera Corporation". *Biotech Business Week, pp.* 1540 (2007-09-17).) Squalamine is also marketed under the brand name Squalamax™ as a dietary supplement, though it has not been approved as a drug in this form and thus cannot make therapeutic claims. Squalamax™ is an unfractionated extract of shark liver, containing innumerable uncharacterized substances in addition to squalamine, itself present below 0.01% of the total weight of the extract. ("Cyber Warning Letter", Center for Drug Evaluation and Research (2002-05-06), http://www.fda.gov/CDER/warn/cyber/2002/CFSANnuGen.htm; Retrieved 2009-03-31.) Moreover, the dietary supplement form of squalamine is not pharmaceutical grade squalamine, which requires significantly greater manufacturing efforts.

By 2006, over 300 patients had received squalamine in doses ranging from 6-700 mg/m2/day by iv administration, in three Phase I and nine Phase II studies (Hao et al., "A Phase I and pharmacokinetic study of squalamine, an aminosterol angiogenesis inhibitor," Clin Cancer Res 9, 2465-71 (2003); Herbst et al., "A phase I/IIA trial of continuous five-day infusion of squalamine lactate (MSI-1256F) plus carboplatin and paclitaxel in patients with advanced non-small cell lung cancer," Clin Cancer Res 9, 4108-15 (2003); Bhargava et al., "A phase I and pharmacokinetic study of squalamine, a novel antiangiogenic agent, in patients with advanced cancers," Clin Cancer Res 7, 3912-9 (2001); and Connolly et al., "Squalamine lactate for exudative age-related macular degeneration," Ophthalmol Clin North Am 19, 381-91, vi (2006). The studies showed that the compound exhibited an acceptable safety profile and evidence of efficacy in these early trials. In 2006 development of squalamine was halted for economic/strategic reasons by Genaera, and has remained in a dormant stage since.

There is a need in the art for new treatments for viral infections. There are a wide variety of viral diseases having limited or ineffective treatments. The present invention addresses the problem by providing a new method of treating and/or preventing viral infections.

SUMMARY OF THE INVENTION

The present invention is directed to methods of treating and/or preventing viral infections comprising administering a therapeutically effective amount of squalamine or a derivative thereof, an isomer or prodrug of squalamine, or a pharmaceutically equivalent salt thereof to a subject, such as a mammal, in need. A "subject in need" is a human or animal at risk of a viral infection, or which has contracted a viral infection. Preferably, the squalamine is a pharmaceutical grade squalamine. Preferably, the squalamine or derivative thereof is a pharmaceutical grade of squalamine, and the composition can further comprise one or more pharmaceutically acceptable excipients. The squalamine or derivative thereof is present in an amount sufficient to produce an antiviral effect.

In another embodiment, the invention encompasses methods of treating and/or preventing viral infections comprising administering a therapeutically effective amount of an aminosterol that can inhibit the formation of actin stress fibers in endothelial cells stimulated by a ligand known to induce stress fiber formation, having the chemical structure of Formula I:

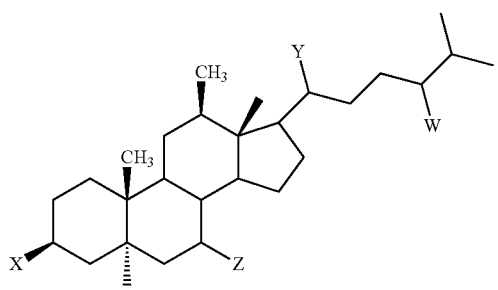

wherein,
W is 24S—OSO$_3$ or 24R—OSO$_3$;
X is 3β-H$_2$N—(CH$_2$)$_4$—NH—(CH$_2$)$_3$—NH— or 3α-H$_2$N—(CH$_2$)$_4$—NH—(CH$_2$)$_3$—NH—;
Y is 20R—CH$_3$; and
Z is 7α or 7β-OH In yet another embodiment of the invention, the aminosterol is a derivative of squalamine modified through medical chemistry to improve biodistribution, ease of administration, metabolic stability, or any combination thereof. In another embodiment, the squalamine or aminosterol is modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system.

In certain embodiments of the invention, the methods comprise administering squalamine or a derivative thereof at an effective daily dosing amount of about 0.1 to 20 mg/kg body weight. In other embodiments, the effective amount is administered in a regimen that achieves and maintains a tissue concentration of squalamine in body organs and tissues of between about 0.1-200 µg/gram (tissue wet weight).

The composition can be administered via any pharmaceutically acceptable method, including but not limited to intravenously, subcutaneously, intramuscularly, topically, orally, or by inhalation.

In one embodiment of the invention (a) the composition does not demonstrate an altered IC$_{50}$ or IC$_{90}$ (drug concentration required to inhibit viral growth by 50% or 90% respectively) over time; (b) the composition demonstrates an IC$_{50}$ or IC$_{90}$ which does not increase by more than 0%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, or 30% over time; (c) the composition demonstrates an IC$_{50}$ or IC$_{90}$ which does not increase by an amount described in (b) over a time period selected from the group consisting of 1 week, 2 weeks, 3 weeks, 4 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1 year, 1.5 years, 2 years, 2.5 years, 3 years, 3.5 years, 4 years, 4.5 years, and 5 years; or (d) any combination thereof.

The viral infection to be treated or prevented can be caused by any virus, including but not limited to, "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picornaviridae (e.g. Rhinovirus, Poliovirus), Poxyiridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), or any combination thereof. In another embodiment of the invention, the viral infection is caused by a virus selected from the group consisting of herpes, pox, papilloma, corona, influenza, hepatitis, sendai, sindbis, vaccinia viruses, west nile, hanta, or viruses which cause the common cold. In another embodiment of the invention, the condition to be treated is selected from the group consisting of AIDS, viral meningitis, Dengue, EBV, hepatitis, and any combination thereof.

In another embodiment of the invention, the condition to be treated is a chronic disease suspected to be of viral origin.

For example, the condition to be treated can be multiple sclerosis, Type I diabetes, Type II diabetes, atherosclerosis, cardiomyopathies, Kawaski disease, aplastic anemia, etc.

The methods of the invention can further comprise administering the squalamine or derivative thereof in combination with at least one additional active agent to achieve either an additive or synergistic antiviral effect. The additional active agent can be administered concomitantly, as an admixture, separately and simultaneously or concurrently, or separately and sequentially. For example, the additional active agent can be: (a) an antiretroviral agent; (b) nucleoside or nucleotide reverse transcriptase inhibitors (NRTIs); (c) non-nucleoside reverse transcriptase inhibitors (NNRT1s); (d) nucleotide or nucleoside analogues; (e) protease inhibitors (PIs); (f) drugs based on "antisense" molecules; (g) ribozyme antivirals; (h) assembly inhibitors; (i) release phase inhibitors; (j) drugs which stimulate the immune system, such as interferons and synthetic antibodies; (k) fusion inhibitors/gp41 binders; (l) fusion inhibitors/chemokine receptor antagonists; (m) integrase inhibitors; (n) hydroxyurea-like compounds; (o) inhibitors of viral integrase; (p) inhibitors of viral genome nuclear translocation; (q) inhibitors of HIV entry; (r) nucleocapsid zinc finger inhibitors; (s) targets of HIV Tat and Rev; (t) pharmacoenhancers; (u) cytokines; (v) lymphokines; (w) an anti-inflammatory agent; or (x) any combination thereof.

In one embodiment of the invention, described are antiviral compositions comprising at least one squalamine, a squalamine derivative, a squalamine isomer or prodrug, or a pharmaceutically equivalent salt thereof. The compositions can further comprise at least one antiviral immunological adjuvant. Examples of antiviral immunological adjuvants include, but are not limited to corticosteroids, alpha-interferon, etc.

In yet another embodiment of the invention, the composition can further comprise at least one antigen capable of eliciting an immune response. For example, the antigen can be a viral or prion antigen.

In another embodiment of the invention, combination methods of treating or preventing a viral infection are described. The combination methods comprise: (1) administering a therapeutically effective amount of squalamine, a derivative, a squalamine isomer or prodrug, or a pharmaceutically equivalent salt thereof to a subject in need; and (2) administering a conventional antiviral drug. The squalamine composition and conventional antiviral drug can be administered sequentially or simultaneously. If squalamine or a conventional antiviral drug are administered sequentially, either squalamine or the conventional antiviral drug can be administered first.

Also described are compositions comprising (1) at least one squalamine compound, a squalamine isomer or prodrug, or a pharmaceutically equivalent salt thereof to a subject in need; and (2) at least one conventional antiviral drug. The compositions can additionally comprise at least one pharmaceutically acceptable excipient or carrier.

Both the foregoing summary of the invention and the following brief description of the drawings and the detailed description of the invention are exemplary and explanatory and are intended to provide further details of the invention as claimed. Other objects, advantages, and novel features will be readily apparent to those skilled in the art from the following

BRIEF DESCRIPTION OF THE DRAWINGS

FIG. 1: Shows a picture of a cell before (FIG. 1A) and after (FIG. 1B) exposure to squalamine FIG. 1A shows the net negative charge at the cell surface (i.e., green circle) and FIG. 1B shows the change in cell structure following exposure to squalamine. Specifically, squalamine integrates into the cellular membrane, profoundly altering the overall charge of that membrane, and causing displacement of key proteins bound to the membrane through electrostatic interactions and required for actin remodeling to occur.

FIG. 3: Shows the results of a study exploring squalamine's mechanism of action using a cell which expresses two probes, with the effects of treatment noted by comparing the cell before and after exposure to squalamine. The RAW264.7 cell line has been engineered to express a red tagged fluorescent protein ("Lact-C2") that binds avidly to phosphatidylserine. Lact-C2 binds to phosphatidylserine (a negatively charged phospholipid) through highly specific interactions that depend on the "shape" of the phospholipid, rather than its electric charge. In addition the cell line also expresses a green tagged fluorescent cationic fragment ("R-pre"). R-pre binds to phosphatidylserine as a consequence of electrostatic interactions, the strongly positive peptide attracted to the strong negative charges present on the head of phosphatidyl serine. FIG. 3A shows the cells before exposure to squalamine and FIG. 3B shows the cells following exposure to squalamine. As seen in FIG. 3A, before addition of squalamine, both probes are seen to be associated with the plasma membrane of the cells, as expected. Following exposure of these cells to squalamine (80 µM, 30 minutes), R-pre was displaced from its residence on the plasma membrane to other areas within the cell's interior. In contrast, exposure of these cells to squalamine did not alter the localization of Lact-C2. This experiment supports the hypothesis that squalamine, a positively charged molecule, neutralizes the negatively charged phospholipids upon entry into the membrane, and can, as a consequence, cause the displacement of membrane proteins bound by virtue of electrostatic interactions.

FIG. 4: Shows the results of an in vivo test to determine the effectiveness of squalamine against Yellow Fever in Syrian hamsters. Squalamine was administered to infected Syrian hamsters at 0.7, 2.5, and 7.7 mg/kg once daily achieving an antiviral effect. At 7.7 mg/kg/day, 60% survival was observed, similar to the survival achieved with administration of ribivarin, 50 mg/kg/day, and compared to the 20% survival seen in animals receiving a placebo (saline).

FIG. 8: Shows the results of an in vivo test to determine the effectiveness of squalamine against Eastern Equine Encephalitis virus in Syrian hamsters. Squalamine administered at 10 mg/kg/day, s.c., is shown to increase survival, compared with a vehicle control.

FIG. 9: Shows the results of an in vivo test to determine the effectiveness of squalamine against Eastern Equine Encephalitis virus in Syrian hamsters. Squalamine administered at 10 mg/kg/day s.c. is shown to significantly reduce viremia compared with a vehicle control, in the experiment described in FIG. 8.

DETAILED DESCRIPTION OF THE INVENTION

Figure 2:
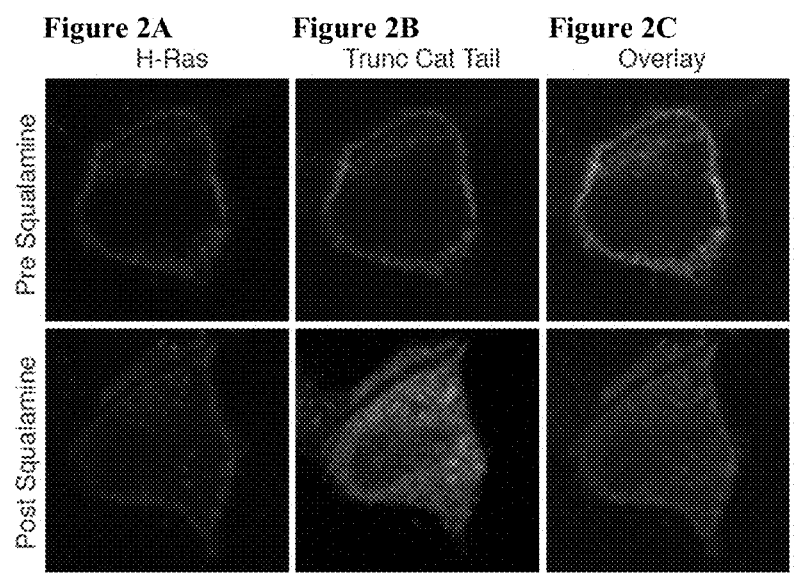
FIG. 2: Shows microscopic visualization following transfection of a RAW 264.7 macrophage line with engineered recombinant vectors to generate cells that expressed two peptide probes, each linked to a red (FIGS. 2A and 2D) or green (FIGS. 2B and 2E) fluorescent protein. "Trunc Cat Tail" (GFP-ARDGRRRRRRARARCVIM) is a highly cationic probe, that associates with the plasma membrane through electrostatic forces. "H-Ras" (RFP—full length H-Ras) is a member of the Ras family of proteins that associates with the plasma membrane predominantly through hydrophic forces. Prior to exposure of these cells to squalamine, both H-Ras and Trunc Cat Tail can be seen associated with the plasma membrane (FIGS. 2A, 2B, and 2C). Following the addition of squalamine (10 micromolar) to the culture medium in which the cells are bathed, the True Cat Tail probe is displaced into the cytoplasm, while the H-Ras probe remains associated with the membrane (FIGS. 2D, 2E, and 2F).

The present invention is directed to methods of treating and/or preventing viral infections comprising administering a therapeutically effective amount of squalamine, an isomer or prodrug of squalamine, a squalamine derivative, or a pharmaceutically equivalent salt thereof to a subject in need. A "subject in need" is a human or animal at risk of a viral infection, or which has contracted a viral infection.

A variant or derivative of squalamine may have one or more chemical modification which do not modify the antiviral activity of squalamine A "variant" or "derivative" of squalamine is a molecule in which modifications well known in the art of medicinal chemistry to "mimic" the original spatial and charge characteristics of a portion of the original structure have been introduced to improve the therapeutic characteristics of squalamine. In general, such modifications are introduced to influence metabolism and biodistribution. Examples of such variants or derivatives include, but are not limited to, (1) substitutions of the sulfate by a sulfonate, phosphate, carboxylate, or other anionic moiety chosen to circumvent metabolic removal of the sulfate moiety and oxidation of the cholesterol side chain; (2) replacement of an hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system. As used herein, the term "squalamine" is intended to encompass squalamine and variants or derivatives thereof.

In another embodiment, the invention encompasses methods of treating and/or preventing viral infections comprising administering a therapeutically effective amount of an aminosterol that can inhibit the formation of actin stress fibers in endothelial cells stimulated by a ligand known to induce stress fiber formation, having the chemical structure of Formula I:

wherein,
W is 24S—OSO$_3$ or 24R—OSO$_3$;
X is 3-βH$_2$N—(CH$_2$)$_4$—NH—(CH$_2$)$_3$—NH— or 3α-H$_2$N—(CH$_2$)$_4$—NH—(CH$_2$)$_3$—NH—;
Y is 20R—CH$_3$; and
Z is 7α or 7β-OH To date, a hypothesis that explains the diversity of squalamine's effects has not been reported. While not wishing to be bound by any particular theory, the inventor believes that squalamine exerts its effects by interrupting a key step in the pathways involved in actin dynamics, which it achieves by an unprecedented mechanism. Squalamine does so by integrating in the cellular membrane, profoundly altering the overall charge of that membrane, and causing displacement of key proteins bound to the membrane through electrostatic interactions and required for actin remodeling to occur. Thus, upon entry into a cell, squalamine profoundly alters the behavior of the circuitry involved in control of the actin cytoskeleton. Most viruses must exert control over the actin cytoskeleton to gain entry into the cell they target. This alteration by squalamine effectively "closes the door" to viral entry into the cell. This is because a substance that interrupts the actin remodeling circuitry of a target cell utilized by a virus for infection makes the cell "resistant" so long as the disruptive effects persist.

The basic mechanism of action of squalamine should be operative in any cell into which squalamine can gain entry. Thus, squalamine can prevent viral infection of any cell into which squalamine can gain entry. Moreover, because of the broad tissue distribution of squalamine, the compound can alter the virulence of a virus by interfering with its infectivity of any number of tissues in the animal, a "whole animal" effect that might be missed in a simple cellular screen. Indeed, squalamine represents a class of antiviral that achieves its therapeutic effect by creating a state of viral resistance within the treated animal, rather than by directly targeting a viral enzyme or protein. During this period of squalamine resistance, viral particles, unable to infect tissues, would be cleared and destroyed by the cellular mechanisms that are normally engaged to dispose of particles of their size and composition (i.e., phagocytic destruction by neutrophils, macrophages, and the reticuloendothelial system). Furthermore, as a consequence of the mechanism proposed for the antiviral activity of squalamine, which involves inhibition of cellular circuitry used by viruses to remodel the actin cytoskeleton to permit invasion, squalamine would be expected to exhibit a very broad spectrum of activity, covering viruses of all classes, regardless of their genome composition (RNA vs DNA viruses).

In the case of squalamine, the "resistance" state should last as long as the compound persists in circulation, that being several hours. Based on the known pharmacokinetics of squalamine in rodents, dogs and humans, following administration the compound should rapidly gain entry to a wide range of cells, remain in intracellular sites for between minutes to hours, and eventually traffic out of the cell, unmetabolized, re-entering the circulation, to then be transported into the hepatocyte via its basolateral surface, passage through the cell and subsequently transported from the apical surface of the hepatocyte into the biliary tract.

FIGS. 1A and 1B show the physical changes in cell structure upon exposure to squalamine More particularly, FIG. 1A shows a picture of a cell before exposure to squalamine. The net negative charge of the cytoplasmic face of the plasma membrane at the cell surface is clearly depicted by virtue of the adherence of the green fluorescent positively charged probe, which creates a green outline at the cell's periphery. After exposure to squalamine, as shown in FIG. 1B, squalamine integrates into the cellular membrane, profoundly altering the overall charge of that membrane, and causing displacement of key proteins bound to the membrane through electrostatic interactions and required for actin remodeling to occur. The green cationic probe, displaced from the membrane surface as a consequence of the neutralization of the negative charge, diffuses into the cytoplasm, filling the cell with a green color. It is this change in the cell structure which inhibits viral infection of the cell. Specifically, viruses seek the negatively charged cell surface as a "gateway" to the cell for infection. Squalamine effectively closes the gateway by changing the charge and structure of the cell membrane.

Lack of Resistance: Antiviral drug resistance is a significant problem encountered with treating and preventing viral infections. Antiviral resistance means that a virus has changed in such a way that the antiviral drug is less effective in treating or preventing illnesses caused by the virus. Virally encoded drug resistance has been documented against nearly all compounds with antiviral activity. Drug resistance is defined as a reduced susceptibility to a drug in a laboratory culture system and is expressed as an altered $IC_{50}$ or $IC_{90}$ (drug concentration required to inhibit viral growth by 50% or 90% respectively). This is termed the phenotype. This phenotype is determined by specific mutations in the viral genome (the genotype), which leads to alterations in the viral target protein (for example, HIV reverse transcriptase) or the viral drug activator (for example, herpes simplex thymidine kinase). The high rate of replication of some viruses determines that many of these genetic variants will already exist in untreated infected people. This is consequent on an inherent error rate of viral polymerases, especially for RNA viruses such as HIV and influenza, which replicate the viral genome. A wide range of viral variants, including those with mutations associated with drug resistance, will therefore be present. This collection of variants in one person is termed the viral quasispecies, with the "fittest" virus representing the majority population. The use of an antiviral drug will provide a selective pressure for the preferential growth of variants with a reduced susceptibility to drugs in accordance with Darwinian evolutionary principles. The emergent drug resistant virus will be the fittest in the presence of drug. Some drug resistant viruses, however, seem not to replicate as well as wild type virus (in the absence of drug). In some cases, multiple mutations are required for the development of high level resistance, and insufficient suppression of viral replication by antiviral drugs will predispose to their sequential acquisition. Pillay et al., "Antiviral drug resistance," *Public Health Laboratory Service Antiviral Susceptibility Reference Unit, Division of Immunity and Infection, University of Birmingham Medical School, Birmingham B15 2TT*, http://www.bmj.com/content/vol317/issue7159/fulltext/supplemental/660/index.shtml, accessed on Oct. 21, 2009.

In contrast to traditional antiviral therapies, viruses are not expected to develop resistance to squalamine. This is because unlike conventional antiviral therapies, squalamine does not act upon a single mechanism by which a virus infects a cell. Rather, squalamine changes the cell structure for a period of time during which the virus cannot infect the cell. In contrast, certain anti-HIV drugs target the CD4 receptor and other antiviral drugs target inhibition of replication. Viral variants can circumvent each of these targeted antiviral therapies. In one embodiment of the invention, squalamine does not demonstrate an altered $IC_{50}$ or $IC_{90}$ (drug concentration required to inhibit viral growth by 50% or 90% respectively) over time. In other embodiments of the invention, squalamine demonstrates an $IC_{50}$ or $IC_{90}$ which does not increase by more than 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, or 30% over time. In other embodiments of the invention, the time period over which the change in $IC_{50}$ or $IC_{90}$ (or lack thereof) is measured is 1 week, 2 weeks, 3 weeks, 4 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1 year, 1.5 years, 2 years, 2.5 years, 3 years, 3.5 years, 4 years, 4.5 years, or 5 years.

Toxicity: Conventional antiviral agents are generally designed to target viral specific enzymes, such as RNA and DNA polymerases, proteases, or glycosidases; as a consequence the drug inhibits the activity of the viral enzyme to a far greater extent than it does to analogous human enzymes, required for normal cellular functioning. In many instances toxicity develops as a consequence of the residual activity of the agent towards the analogous enzymes of the host. The experience collected to date involving the administration of squalamine to humans suggests that the compound has an acceptable therapeutic index, a property that further enhances the utility of the invention disclosed herein.

I. Definitions

The following definitions are provided to facilitate understanding of certain terms used throughout this specification.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the phrase "therapeutically effective amount" shall mean the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

II. Mechanism of Squalamine's Antiviral Activity

A. The Relationship Between Squalamine and Membrane Electrostatic Potential

Squalamine is a cationic (net positively charged) aminosterol. It possesses a negatively charged sulfate group on its cholesterol side chain that contributes a single negative charge; however, it also possesses the polyamine spermidine attached to the opposite side of the molecule. This moiety has three positively charged amino groups (at physiological pH). Overall, therefore, squalamine exhibits a net positive charge of 2, and these charges are localized to a specific region of the molecule, that being the polyamine Because of its net positive charge and amphilicity, squalamine partitions into membranes of appropriate composition and interacts electrostatically with negatively charged phospholipids within the membrane. Thus, upon partitioning into a membrane, squalamine is expected to reduce the net negative charge of the membrane. Thus, the present invention describes the properties of a cationic lipid (squalamine) which permits safe and effective modification of the cellular membranes of a tissue or organ in such a fashion as to reduce the capacity of the tissues or organs to be infected by a virus. Additionally, the invention describes the discovery of specific cellular transporters that either restrict or facilitate the passage of an aminosterol into a tissue or organ, knowledge which can direct the application of the invention to specific viral infections.

It has been only recently appreciated that membrane surfaces present within the interior of animal cells exhibit a net negative surface charge, also referred to as "a net negative electrostatic potential". This net negative charge results from the presence of specific anionic phospholipids that comprise these membrane surfaces. For example, the anionic phospholipid, phosphatidylserine, is the most abundant anionic phospholipid in animal cells, is present on the inner surface of the plasma membrane of animal cells, and is the principal lipid responsible for the negative electrostatic charge of the inner layer of the plasma membrane (McLaughlin and Murray 2005; Yeung, Terebiznik et al. 2006; Steinberg and Grinstein 2008; Yeung, Gilbert et al. 2008). Similarly, phosphatidylserine is present in other intracellular membranous locations, such as the endosomes and the Golgi apparatus, but in lesser proportions than observed for the plasma membrane, and thus, conferring a weaker overall negative charge on these internal membranes. An excellent review on the role of anionic phospholipids in establishing the negative electrostatic potential of cellular membranes has been recently published (Steinberg and Grinstein 2008).

The negative electrostatic potential of intracellular membranes is now believed to play a major role in the physical positioning of many intracellular proteins that physically associate with intracellular membranes (McLaughlin and Murray 2005; Yeung, Terebiznik et al. 2006; Steinberg and Grinstein 2008; Yeung, Gilbert et al. 2008). It has been discovered that many proteins involved in important cellular functions are themselves positively charged, and as a consequence of electrostatic interactions, are directed to negatively charged membranes where they are positioned appropriately to execute their functions. Of particular note are the many small GTPases involved in intracellular signaling. In particular, the RhoGTPases, including Rac and Cdc 42, which play a central role in the dynamics of the actin cytoskeleton of all eukaryotic cells, are tethered to the inner surface of the plasma membrane via electrostatic interactions (Kelly 2005; Yeung, Terebiznik et al. 2006; Yeung, Gilbert et al. 2008).

Squalamine can reduce the negative electrostatic potential of the cytoplasmic surface of a cell and displace proteins associated via electrostatic forces. Specifically, based on the cationic character of squalamine and the importance of electrostatics in the association of key proteins with the inner surface of the plasma membrane, it is expected that upon exposure of a cell to squalamine, and its subsequent entry into the plasma membrane, proteins associated with the cytoplasmic surface via electrostatic interactions will be displaced and released into the cellular cytoplasm.

As demonstrated in the Examples below, squalamine can reduce the net electrostatic potential of cellular membranes into which it enters. Remarkably, it does so without disrupting the physical integrity of the membranes into which it integrates. This striking property of squalamine is likely a result of the manner in which squalamine positions itself on the membrane. Analysis of its structure would suggest that squalamine lies superficially on the surface of the membrane, interacting electrostatically with the lipid headgroups at the aqueous interface, rather than by burying itself within the lipid phase. As a consequence, squalamine can displace proteins normally positioned via electrostatic interactions on the plasma membrane and other membranes to which squalamine is known to traffic without directly disrupting the physical integrity of the membrane.

As demonstrated in the literature, reduction in the electrostatic potential of the plasma membrane of the magnitude required to displace Trunc Cat Tail and R-pre (see e.g., Example 1) should be sufficient to cause displacement of many of the GTPases known to be associated with the plasma membrane. In particular, it is reasonable to highlight Rac1 and Cdc 42, two GTPases known to be anchored through phosphatidylserine based interactions (Kelly 2005; Finkielstein, Overduin et al. 2006; Yeung, Terebiznik et al. 2006; Yeung, Gilbert et al. 2008). These Rho GTPases play a central role in the dynamics of the actin cytoskeleton of all eukaryotic cells. These dynamics come into play when cells migrate, during endocytosis, in the processes of membrane ruffling, filopodia formation, and so on.

Indeed, the results of Example 1 suggest a mechanism to explain certain inhibitory effects of squalamine on the endothelial cell, such as migration, growth factor dependent stress fiber formation, and the formation of focal adhesion contacts, each an actin based process (Sills, Williams et al. 1998; Williams, Weitman et al. 2001).

Relevant to the present invention, the Rho GTPases, as key components in the dynamic remodeling of the actin cytoskeleton, are known to be critically involved in numerous events in the life cycle of most, if not all, known animal viruses (Pelkmans, Fava et al. 2005; Mercer and Helenius 2008), including Vaccinia and small pox, West Nile virus, influenza, yellow fever, dengue, Adenoviruses, Rubella, and HIV. Displacement of these RhoGTPases from the plasma membrane, resulting in their functional inactivation, would necessarily result in perturbation of the life cycle of a virus, and thereby reduce its infectivity. In this state, the squalamine treated cell would appear resistant towards all viruses that required these Rho GTPases for infection.

B. Viral Infection, Anionic Phospholipids, and Electrostatic Potential

Viruses must deliver their genomes into a target cell. They accomplish this ultimately by fusing with the plasma membrane of the cell. Viruses surrounded by membranes can fuse directly with the membrane of a cell. Alternatively, both enveloped and non-membrane enclosed viruses can be engulfed by an endocytic process. Escape from the endosomal compartment requires a fusion event between the viral envelope or its membrane to permit the viral genome to gain entry into the cell's interior. These events in the life cycle of all viruses are known to engage cellular machinery involved in actin cytoskeletal remodeling. Indeed, viral infectivity is now known to be sensitive to inhibition by agents that disrupt the normal functioning of actin remodeling machinery. By altering the electrostatic potential of the inner surface of a cell, and consequently disturbing the association of proteins required for the normal dynamics of actin cytoskeletal remodeling, squalamine should influence actin dynamics involved in efficient viral infection.

Viral entry and infection, involving membrane fusion, viral uptake and internalization, appear to be exceedingly sensitive to the presence of adequate amounts of cellular anionic phospholipid, especially phosphatidylserine (Coil and Miller 2005; Coil and Miller 2005; Mercer and Helenius 2008). Indeed, most, if not all cells, appear to have insufficient phosphatidylserine to support maximal viral infectivity (Coil and Miller 2004; Coil and Miller 2005; Coil and Miller 2005). Hence, adding exogenous phosphatidylserine to a wide range of cell types increases the viral infectivity of a wide range of virus. Conversely, cells that are genetically deficient in phosphatidylserine (and require exogenous phosphatidylserine for survival) appear to become less capable of supporting viral infection as total cellular stores of phosphatidylserine decrease (Kuge, Akamatsu et al. 1989). Precisely why the cellular content of phosphatidylserine should be rate limiting for many (if not all) viruses is not well understood (Coil and Miller 2004; Mercer and Helenius 2008). However, since squalamine is known to complex with phosphatidylserine in membranes, the presence of this aminosterol would effectively reduce the free concentration of phosphatidylserine within the cell, effectively depleting a cellular lipid critical for viral infectivity.

C. Squalamine is a Substrate for the Organic Cation Transporters Oct 1-3

Squalamine, an ionic compound with a strong negative charge (provided by the sulfate moiety) and three strong positive charges (provided by the protonated spermidine), would not be expected to enter cells freely by permeating or diffusing through the plasma membrane. Molecules such as these generally enter cells via interactions with transporting proteins situated on the plasma membrane. Furthermore, although squalamine could interact directly with anionic phospholipids and subsequently integrate into the cellular membrane, cells do not normally expose anionic phospholipids on the outer leaflet of the plasma membrane, the surface exposed to the "outside world". As pointed out above, it is the inner surface of the plasma membrane that normally bears a negative electrostatic potential.

To date, no published data exist that describes the transporters that the aminosterols must utilize to enter cells. Knowledge of the transporters utilized by specific aminosterols permits prediction of the tissues and organs these compounds will enter following administration to an animal. In the present invention, knowledge of the tissue distribution of the specific transporters utilized by squalamine could guide the choice of viral infections to treat.

The net cationic charge and amphipathic character of squalamine suggest that it could be a substrate for the principal organic cation transporters currently identified as responsible for the pharmacokinetic trafficking of organic cations, the recently described transporters, Oct1-3 (Hayer-Zillgen, Bruss et al. 2002; Slitt, Chemington et al. 2002; Koepsell 2004; Koepsell and Endou 2004; Alnouti, Petrick et al. 2006). Example 3 below demonstrates that squalamine is a substrate for the known Oct 1-3 transporters, suggesting that squalamine has a greater opportunity for entering all tissues and organs of the body, since one or another of these transporters in universally expressed. For example, squalamine should be capable of entering brain microvascular capillaries, since Oct2 is known to be expressed in those cells (Sung, Yu et al. 2005). In contrast, Aminosterol 1436 is recognized solely by Oct3, which is most abundantly expressed in placenta and heart, and the least abundantly expressed of the transporters. As shown in Example 3, while squalamine readily accumulates within endothelial cells, Aminosterol 1436 does not.

Given the results of Example 4 below, showing that entry of squalamine into the human umbilical vein endothelial cell (HUVEC) is over 2 orders of magnitude greater than for Aminosterol 1436, reflecting the difference in transporter affinities expressed by the endothelial cell specific for the two aminosterols, and demonstrating that Aminosterol 1436 does not appear to enter endothelial cell, it becomes apparent that to predict whether a tissue or organ could accumulate amounts of Aminosterol 1436 required to achieve a therapeutic benefit, one would need know whether Oct3 was expressed in those tissues and organs, and the magnitude of expression of the transporter.

The discovery that squalamine is recognized by each of the known Oct transporters provides a rationale for considering the use of squalamine for a wide variety of viruses, regardless of their particular tissue or organ tropism.

D. Squalamine, Access to Endothelial Cells, and Viral Infections

Because it is known that endothelial cells express Oct transporters, and that the vascular and hepatic sinusoidal endothelium are cell types targeted by most if not all viruses that cause systemic disease in animals, such as Hantaviruses (Geimonen, Neff et al. 2002) (Hantaviruses cause two human diseases: hemorrhagic fever with renal syndrome (HFRS) and hantavirus pulmonary syndrome (HPS)), Hepatitis B virus (Breiner, Schaller et al. 2001; Rong, Huang et al. 2007), Yellow fever virus (Khaiboullina, Rizvanov et al. 2005), Dengue fever (Luplertlop and Misse 2008), Varicella-Zoster (Nikkels, Debrus et al. 1995), influenza virus (Feldmann, Schafer et al. 2000; Klenk 2005; Sumikoshi, Hashimoto et al. 2008; Yao, Korteweg et al. 2008), Reovirus (Verdin, King et al. 1989), Nipah Virus (Wong, Shieh et al. 2002), human rotavirus (Morrison, Gilson et al. 2001), Parvovirus (Bultmann, Klingel et al. 2003) (e.g., parvovirus B19 (PVB19)-associated diseases), Cytomegalovirus (Carlson, Chang et al. 2005), Vaccinia (Liu, Xu et al. 2005), Hepatitis C (Balasubramanian, Munshi et al. 2005), HIV (Bashirova, Geijtenbeek et al. 2001), Ebola (Hensley and Geisbert 2005), squalamine would be expected to exert antiviral benefit at both the level of the tissues that comprise organs as well as within the vascular network of the body as a whole.

Furthermore, knowledge of the transporters that recognize squalamine could provide guidance in the dosing regimens required to most effectively utilize squalamine as an antiviral therapeutic. For example, it is known that certain individuals who have inherited a genetic variant of the Oct1 transporter require higher doses of metformin (a drug transported into the liver by Oct1) to maintain normal blood sugar, as compared to those who express the "wild type" transporter (Reitman and Schadt 2007). Similarly, only Oct1 is significantly expressed in unstimulated human CD4 positive T lymphocytes, the target cell of HIV, while Oct2 expression is not observed, and Oct3 only after cytokine stimulation, suggesting that squalamine would be taken up into white blood cells commonly targeted by many human viruses and predictably exert its antiviral effects in those cells (Minuesa, Purcet et al. 2008).

E. Use of the Endothelial Cell Assay to Screen Active Squalamine Analogs

It has been well described in the literature that squalamine inhibits numerous actin-dependent processes of vertebrate endothelial cells, when these cells are exposed to non-cytotoxic concentrations of the molecule (Sills, Williams et al. 1998; Williams, Weitman et al. 2001) (Li, Williams et al. 2002). For squalamine to exert such an effect it must necessarily: (1) enter the cell, (2) achieve sufficient concentrations to influence the dynamics of the process being measured, and (3) reduce the electrostatic potential of the inner surface of the plasma membrane to an extent the results in the displacement of proteins, such as the RhoGTPases, required for dynamic regulation of the actin cytoskeleton.

It is possible to adapt an observation reported in the literature for the purpose of screening for derivatives of squalamine that can effectively reduce the electrostatic potential of the plasma membrane of a cell, a property that is required for the antiviral activity of squalamine. The basic screening assay involves measurement of the effect of the analog on actin stress fiber formation in endothelial cells following stimulation with VEGF or thrombin or any other stimulant known to induce stress fiber formation in endothelial cells. In this assay, stress fiber formation can be monitored by any method that visualizes their presence, either directly (fluorescence imaging) or indirectly (such as the measurement of the activity of enzymes or the appearance of phosphorylated proteins, like myosin light chain kinase, and myosin light chain, respectively).

A squalamine derivative or isomer that can effectively reduce the negative electrostatic potential of the plasma membrane by a magnitude that releases proteins anchored by electrostatic forces, should inhibit Rho GTPase dependent processes, such as growth factor-dependent stress fiber formation in endothelial cells. Example 5, below, describes a screening method to identify derivatives or isomers of squalamine that exhibit comparable in vitro properties on the dynamics of the actin cytoskeleton in the endothelial cell. The basic methods have been published (Williams, Weitman et al. 2001). The aminosterols evaluated were squalamine and several derivatives and isomers (Compounds A-G), the structures of which are shown in FIG. 4. The results, summarized in Table 3 below, showed that squalamine and the squalamine related compounds A, B, and C disrupt thrombin induced stress fiber formation. This activity was not observed for squalamine analogs D, E, F, and G.

As seen in Table 4, certain stereo-isomers of squalamine, such as the 3-α isomer (Compound A), the 24 S isomer (Compound B), and the 7β hydroxy isomer (Compound C), each inhibited thrombin-induced stress fiber formation. In contrast, aminosterols D-G were inactive. Compound D, a stereoisomer of squalamine, which differs from squalamine at a single stereo-center ($C_{20}$) was inactive in the thrombin induced stress fiber formation assay. The results of Example 5 demonstrate that only certain isomers of squalamine can enter cells, reduce electrostatic potential, and disturb actin cytoskeletal dynamics.

The antiviral properties of squalamine and analogs thereof disclosed herein are believed to depend upon the ability of the aminosterol to both enter cells and also neutralize the negative electrostatic potential of the inner surface of the plasma membrane to a degree that causes release of proteins anchored electrostatically to the plasma membrane. Hence, only those compounds that can inhibit growth-factor induced stress fiber formation as monitored in the in vitro assay above, would be expected to exhibit antiviral via the mechanism proposed for squalamine.

F. Squalamine can Effectively Prevent Yellow Fever Infection

An example of the use of squalamine to prevent a viral infection in vivo is presented in Examples 6-7 below, which demonstrate the antiviral activity of squalamine against Yellow Fever in the hamster, a model of Yellow Fever that resembles the human infection. In FIG. 4 squalamine is administered prior to viral infection via an intraperitoneal route, while in FIG. 5 dosing is subcutaneous. Squalamine administered at a dose of 7 mg/kg/day i.p. achieved survival comparable to ribavirin, dosed optimally for this infection, at 50 mg/kg/day (FIG. 4), compared with placebo-treated animals that achieved a survival of 25%. In the example illustrated in FIG. 5, a single daily dose of squalamine at 15 mg/kg/day administered s.c. through day 6 post infection resulted in 70% survival, compared with 40% survival with ribavirin treatment dosed via a single daily injection of 32 mg/kg/day over the same period, and where placebo treated animals achieved a survival of 15%.

Yellow fever is a member of the Flaviviridae, which includes Hepatitis C, Dengue Fever Virus, Japanese Encephalitis Virus, Tick Borne Encephalitis Virus, Bovine Viral Diarrheal Virus, Classical Swine Fever Virus, Border Disease Virus, and Hepatitis G virus (Leyssen, De Clercq et al. 2000). To date only a limited number of substances have proven effective in this model. They include antiviral nucleoside analogs such as ribavirin and interferon-alpha (Sbrana, Xiao et al. 2004). The experimental model used in Example 6 has been published in detail (see e.g., Tesh, Guzman et al. 2001; Xiao, Zhang et al. 2001) and used in the evaluation of antiviral therapeutics (Sbrana, Xiao et al. 2004).

G. Squalamine can Effectively Treat a Yellow Fever Infection

Figure 6:
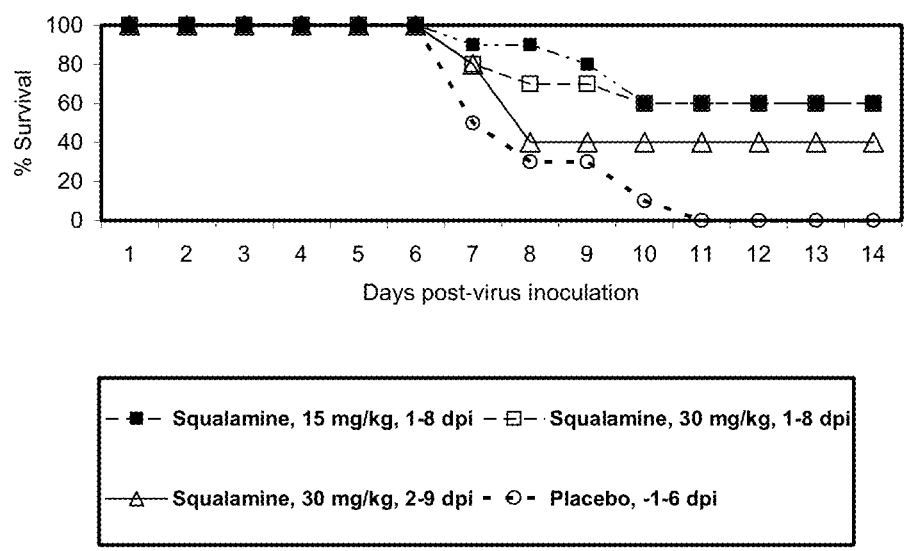
FIG. 6: Shows the results of an in vivo test to determine the effectiveness of squalamine against an established Yellow Fever in Syrian hamsters. Squalamine treatment is shown to cure a lethal infection when administered 1 or 2 days after viral administration.

An antiviral therapeutic of greatest utility should have the capacity to treat (and cure) an existing viral infection, i.e., when the individual is already suffering from the illness. With respect to Yellow Fever, no effective therapeutic has as yet been developed for human infection. An example of the utility of squalamine in the treatment of an existing viral infection is presented in Example 8. To determine whether squalamine can treat an existing Yellow Fever infection in the hamster model, animals were infected with a lethal inoculum of virus, and then begun on once daily treatment with squalamine (15 mg/kg/day, or 30 mg/kg/day s.c.) beginning on day 1 or day 2 after viral administration and continuing until day 8 and 9, respectively. Survival was monitored, and animals that remained alive by day 21 were considered "cured." By day 11, 100% of untreated animals had died. In contrast, of the animals that had received 15 mg/kg/day (from day 1-day 8) or 30 mg/kg/day (from day 1-day 8) 60% were cured. Delay of treatment (30 mg/kg/day) until day 2 and, still resulted in a cure rate of 40% (FIG. 6).

The results of this example demonstrate that squalamine can be utilized as an effective systemic antiviral therapy in already established viral infection. Because of the similarity in the properties shared by the flavivirus family, in addition to Yellow Fever, squalamine could be used to treat infections caused other members of the Flaviviridae including: Dengue, Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

Yellow fever virus utilizes a pH dependent endosomal entry pathway to initiate infection (Pelkmans, Helenius 2003). Based on the mechanism of action of squalamine disclosed in this application and the efficacy of squalamine in the treatment of an established infection caused by Yellow fever, squalamine could be considered for the treatment of other infections caused by viruses that utilize a pH dependent entry pathway such as members of the Orthomyxoviridae including: Influenza A, B, C, Isavirus, Thogotovirus; members of the Rhabdomyoviridae, including: Vesiculovirus, Lyssavirus, Cytorhabdovirus, Nucleorhabdovirus, Novirhabdovirus; members of the Adenoviridae including: all Human Adenovirus types (1-55) and species (A-G), Atadenovirus, Avidenovirus, Icthadenovirus, Mastadenovirus, Siadenovirus; members of the Parvoviridae; members of the Filoviridae; members of the Iridoviridae; the Rubella virus.

H. Squalamine can Effectively Treat a Cytomegalovirus Infection (CMV)

Most viral based therapeutics are developed to inhibit a specific viral target that differs structurally from host cell proteins. Current practice generally involves the crafting of an exquisitely specific "key" to match the highly specific "lock" represented by the viral target; the goal is to increase specificity and minimize activity against host proteins, thereby reducing the toxicity of the compound. As a consequence, most antiviral therapeutics that target the viral pathogen exhibit a narrow spectrum with respect to the viruses against which the compound is active.

By virtue of its mechanism of action disclosed in this application, squalamine should exhibit a very broad spectrum of antiviral activity including both RNA and DNA viruses. An example of its utility in the treatment of an infection caused by a DNA virus is presented in Example 9. Herpes viruses cause many severe human diseases and remain difficult to treat effectively. In example 9 we show the utility of squalamine in the treatment of a systemic infection by Murine cytomegalovirus (MCMV).

Figure 7:
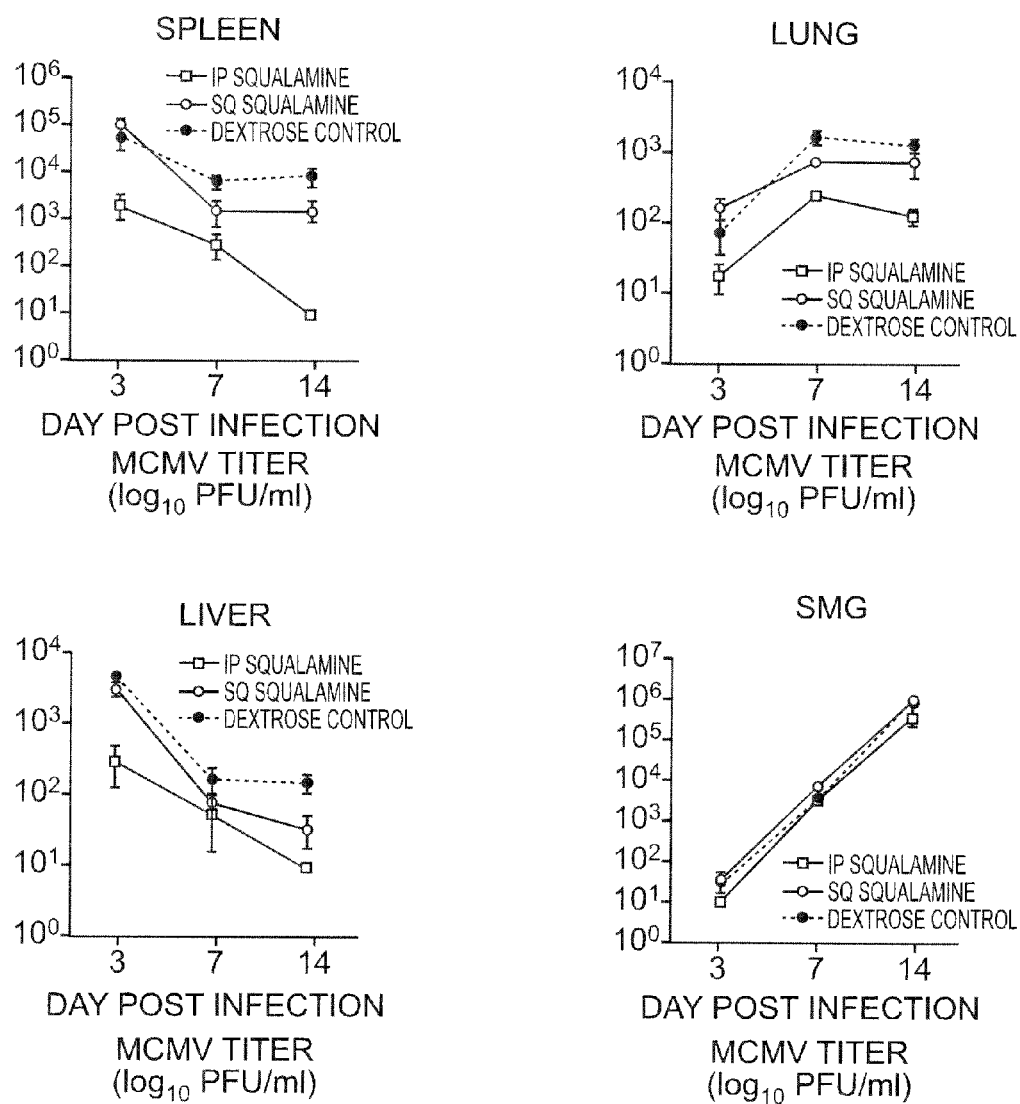
FIG. 7: Shows the results of an in vivo test to determine the effectiveness of squalamine against Cytomegalovirus infection in the mouse. Squalamine, administered at 10 mg/kg/day i.p., is shown to achieve a reduction of viral titers in spleen and liver to undetectable levels in infected animals.

In Example 9 mice were inoculated via the i.p. route with a sublethal inoculum of MCMV. Squalamine was administered at a dose of 10 mg/.kg daily, beginning 1 day prior to infection and continuing daily through day 6, by either the i.p. or s.c. routes, along with an infected cohort that received only vehicle. On days 3, 7, and 14 animals were euthanized and the concentration of virus present in various tissues were measured. Administration of squalamine via the i.p. route, which would have been expected to have resulted in the highest tissue concentrations of the compound, was most effective, resulting in undetectable viral titers in both liver and spleen at day 14 (FIG. 7). Dosing via the subcutaneous route was also effective in reducing viral titers in liver and spleen, but less so than the i.p. route of administration. These results are comparable to the best of the published responses in the mouse MCMV model to highly potent anti-herpes therapeutics currently on the market (Kern 2006; Ruiz, Beadle et al. 2007; Cardin, Bravo et al. 2009).

This experiment also demonstrates that squalamine is active against a member of the Herpesvirus family, and supports its use in infections caused by other members of the Herpes family, including Human cytomegalovirus, Herpes Simplex 1, Herpes Simplex 2, Epstein Barr Virus, Varicella Zoster Virus, Roseolovirus (HHV6 and HHV7), Kaposi's Sarcoma Associated Herpes Virus, Cercopithecine herpesvirus-1, Murine gammaherpesvirus-68, the Bovine Herpesviridae, the Canine Herpesviridae, the Equine Herpesviridae, the Feline Herpesviridae, the Duck Herpesviridae, the Chicken Herpesviridae, the Turkey Herpesviridae, Porcine Herpesviridae and any as yet undiscovered virus subsequently classified as a member of the Herpesviridae.

This experiment also demonstrates, by virtue of the measured reduction in viral titers within the spleen, that squalamine administered systemically can effectively render virally resistant the cells of the spleen that support CMV infection, which include macrophages. This result supports the use of squalamine in the treatment of all viral diseases in which the macrophage is subject to infection.

I. Squalamine Exhibits Antiviral Activity in an Eastern Equine Encephalitis Virus Infection (EEEV), a Potential Bioterror Agent Eastern Equine Encephalitis virus is a member of the Alphavirus family for which neither a vaccine nor an antiviral drug has been developed (Wang, Petrakova et al. 2007). The case fatality rate is between 30-80% for humans and up to 95% for horses and are regarded as a potential biodefense threat (Arrigo, Watts et al. 2008). In Example 8 we show that systemically administered squalamine can reduce viremia in an EEEV infection and improve survival, in a setting where no current therapy has any demonstrable positive effect. Golden hamsters were infected with a lethal inoculum of EEEV via the i.p. route. 1 day prior to infection animals received 10 mg/kg squalamine via subcutaneous dosing, which continued once daily for 6 days post infection. Blood was withdrawn during the first 4 days to monitor viral concentration. Treatment with squalamine extended the survival of the infected animals compared to those receiving vehicle alone (FIG. 8). Viral titers in the blood stream of squalamine treated animals were about 100-fold lower than those receiving vehicle, demonstrating the antiviral activity of the compound when administered systemically (FIG. 9). It would be anticipated that increasing the squalamine dose would increase the therapeutic benefit.

The results of this example demonstrate that squalamine can effectively reduce the concentration of virus in an animal when administered systemically. This experiment also demonstrates the activity of squalamine in treating an infection caused by a member of the Alphavirus family and supports its use in the treatment infection caused by other members of this family, including: Aura virus, Barmah Forest virus, Bebaru virus, Cabassou virus, Chikungunya virus, Eastern equine encephalitis virus, Everglades virus, Fort Morgan virus, Getah virus, Highlands J virus Mayaro virus, Middelburg virus, Mosso das Pedras virus (78V3531, Mucambo virus, Ndumu virus, O'nyong-nyong virus, Pixuna virus, Rio Negro virus, Ross River virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus, Whataroa virus, as well as any as yet undiscovered virus subsequently classified as a member of the Alpaviridae.

J. Squalamine Exhibits Antiviral Activity Against Dengue Virus

Dengue is a flavivirus, responsible for the most prevalent mosquito borne viral infection in the subtropical and tropical regions of the world (Jessie, Fong et al. 2004). At the present time, no antiviral therapeutic has been shown to be effective in humans. Because of the similarity of Dengue virus to the Yellow Fever virus it would be reasonable to assume that Dengue, like Yellow fever, would be sensitive to the antiviral activity of squalamine.

Figure 10:
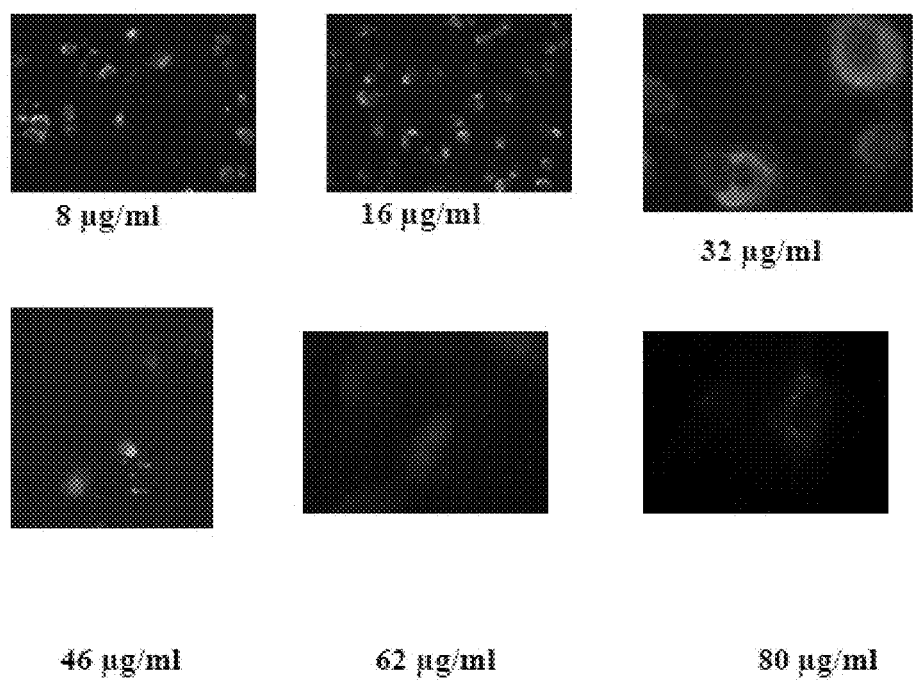
FIG. 10: Shows the results of an in vitro study to assay the antiviral activity of squalamine against Dengue virus. Human microvascular endothelial cells were exposed to Dengue virus in the presence of increasing concentrations of squalamine Viral infection was monitored by immunofluorescent analysis of the Dengue E protein. At 46 ug/ml, squalamine achieved an inhibition of viral infection of about 80%, with 100% inhibition observed at 62 ug/ml.

In Example 11 the antiviral activity of squalamine is demonstrated against Dengue in an in vitro study involving the infection of human microvascular endothelial cells using a published procedure (Zamudio-Meza, Castillo-Alvarez et al. 2009) (FIG. 10). In this experiment cells were exposed to squalamine prior to addition of virus to the system. After a period of time, to permit attachment of virus to the cells, the medium was removed and fresh medium without virus or squalamine was replaced and the cells incubated overnight. Viral infection was monitored immunohistochemically by the presence in the cells a viral protein (the E protein). Squalamine almost completely inhibited viral infection at concentrations above 40 ug/ml, under conditions where cell viability did not appear to be compromised (FIG. 10).

This experiment demonstrates that squalamine has direct antiviral activity against Dengue, a non-enveloped RNA virus of the flavivirus family. Because of the similarity in the properties shared by the flavivirus family, in addition to Yellow Fever and Dengue, squalamine would be expected to be active against Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

K. Squalamine Exhibits Antiviral Activity Against Hepatitis B Virus (HBV)

Hepatitis B virus chronically infects over 350 million people worldwide and is the major cause of liver cancer worldwide. Current therapy, which include interferon used alone or in combination with several nucleoside analogues can suppress the infection in only a fraction of the population and does not achieve a "cure" (Erhardt, Gobel et al. 2009). Clearly, a new agent that could interfere with Hepatitis virus growth would be of utility. In Example 11 the antiviral activity of squalamine against human Hepatitis B virus is described. In this experiment Hepatitis virus was introduced into a culture of primary human liver cells. Squalamine was introduced either at the very start of the infection, or after the infection had progressed for 24 hours, in each case squalamine being present in the system for about 16 hours. Fresh medium was replaced and the cells were maintained in culture for 12 days, after which time the growth of virus was assessed. As described in Example 11, squalamine was effective in inhibiting both the early and later stages of infection of human liver cells by Hepatitis B.

The experiment demonstrates that squalamine can exert antiviral activity against a human Hepatitis B virus infection of human liver. The experiment demonstrates that squalamine can inhibit the early phase of infection as well as the production of virus of cells already infected. These data support the use of squalamine for the treatment of both acute and chronic viral hepatitis caused by Hepatitis B.

L. Squalamine Exhibits Antiviral Activity Against Hepatitis Delta Virus (HDV)

Hepatitis Delta virus is a small RNA virus that generally co-infects individuals already infected with Hepatitis B. About 18 million people are believed to be infected with this virus, for which no drug therapy exists (Abbas, Jafri et al.). In Example 13 the antiviral activity of squalamine against human Hepatitis Delta virus is demonstrated. Squalamine along with HDV was introduced into a culture containing primary human hepatocytes, and exposed to the cells for about 16 hours. Fresh medium was then introduced and the cells maintained in culture for 3 days after which time viral growth was measured quantitatively. Squalamine effectively inhibited the growth of Hepatitis Delta virus in human hepatocytes.

The experiment demonstrates that squalamine can exert antiviral activity against a human Hepatitis Delta virus infection of human liver. These data support the use of squalamine for the treatment of acute and chronic viral hepatitis caused by Hepatitis Delta virus. Since Hepatitis B and D frequently co-infect the same individual, these data would support use of squalamine for the treatment of both infections concurrently.

Squalamine inhibits the replication of both Hepatitis B virus and Hepatitis D virus in primary human hepatocytes, two viruses that differ in their structure, mode of entry, and replicative biology, a result anticipated by the proposed antiviral mechanism of squalamine. These results strongly suggest that squalamine should be effective against other viral infections of the human liver caused by the common Hepatitis viruses: Hepatitis A virus, Hepatitis E, Hepatitis F and Hepatitis G, and any other viral infection of the hepatocyte.

M. Squalamine Exhibits Antiviral Activity Against Human Immunodeficiency Virus (HIV)

Human immunodeficiency virus (HIV), including HIV-1 and HIV-2, can be effectively treated but is not currently curable; in addition, current HIV therapy results in the selection of drug resistant variants (Noe, Plum et al. 2005). Clearly an antiviral therapeutic that exerted antiviral activity by inducing viral resistance within the host cell would be of benefit in a setting where viral mutation and selection of resistant variants posed a therapeutic problem. In Example 14, the antiviral activity of squalamine against HIV is demonstrated, using a published in vitro system (Harmon, Campbell et al.). In this Example HeLa cells have been engineered to express the receptors to which HIV must attach to bind to cells and then gain entry. These cells also contain a reporter gene that is activated upon entry of the HIV virion and serves as the indicator of infection. In this Example squalamine at concentrations around 20 ug/ml effectively inhibited HIV entry while exhibiting no apparent toxicity towards the target HeLa cells.

These data support the use of squalamine for the treatment of HIV and other retroviral infections. In addition these data demonstrate that squalamine can block the infectivity of enveloped viruses, such as HIV, that enter cells via a pH independent fusion process. Thus, these data support the use of squalamine in the treatment of viral infections caused by viruses such as the retroviridae as well as the paramyxoviridae, including: Newcastle disease virus, Hendravirus, Nipah virus, measles virus, Rinderpest virus, Canine distemper virus, Sendai virus, Human parainfluenza 1, 2, 3, 4, mumps virus, Menangle virus, Tioman virus, Tuhokovirus 1,2,3, Human respiratory syncytial virus, avian pneumovirus, human metapneumovirus; viruses such as the picornaviridae, including: Human enterovirus A,B,C,D, Human rhinovirus A,B,C, Encephalomyocarditis virus, Theilovirus, Foot and mouth virus, Equine rhinitis A virus, Bovine Rhinitis B virus, Hepatitis A virus, Human Parechovirus, Ljungan virus, Aichi virus, Teschovirus, Sapeloviris, Senecavirus, Tremovirus, Aviheptovirus; viruses such as the rotoviridae, including: rotavirus A,B,C,D,E; viruses such as the papovaviridae.

The discovery that squalamine and squalamine derivatives and isomers are useful in treating and/or prevention viral infections is unexpected and surprising, given that it is known that squalamine is inhibited from killing bacteria present in the blood stream, by the concentrations of ionized calcium and magnesium present in mammalian blood (supra). Squalamine exerts its antibacterial effects by directly damaging the membranes that surround the microbes. Squalamine binds to these membranes because they are decorated with negatively charged phospholipids that are exposed on the outside of the microbial cell. (Note, that in the case of animal cells, the negatively charged phospholipids are segregated on the inner layer of the membrane, and are not exposed to the environment, or the blood stream). Calcium and magnesium, as cationic ions, bind avidly to the negatively charged phospholipids on the microbial surface and effectively block the sites onto which squalamine must bind. Heretofore squalamine has been demonstrated to exert an anti-viral effect solely by directly damaging the physical integrity of viral membranes, acting like a soap or a disinfectant, and via a mechanism similar to that proposed to explain its antibacterial properties. Based on the body of experimental data that existed prior to the disclosure of this invention, the calcium and magnesium concentrations present in blood, as well as the high albumin binding affinity of squalamine, strongly suggested to those skilled in the art of the development of antiviral compounds that squalamine would not be expected to be an effective in vivo treatment for viral infections. Indeed, no demonstration of squalamine's efficacy as a therapy for a systemic viral infection has been published since the report of the discovery of the molecule in 1993, and since that date no efforts have been undertaken by any academic or commercial entity to develop the compound as an antiviral therapeutic for the treatment of systemic infections.

Moreover, to date, no published study has demonstrated the efficacy of Aminosterol 1436, a molecule closely related structurally to squalamine, in the treatment of any viral infection in an animal. Unpublished studies conducted at the National Institutes of Health with pig-tailed macaques infected with SIV (simian immunodeficiency virus) failed to demonstrate any antiviral benefit from Aminosterol 1436. As described below, this is likely due, in part, to failure of Aminosterol 1436 to access virally infected tissues, a direct consequence of the restricted tissue expression of the specific transporter that permits 1436 to enter specific tissues, as newly disclosed in this invention.

Another benefit of squalamine and squalamine derivatives is that viral resistance is unlikely to occur in the setting of their use. Conventional antiviral drugs, such as the protease inhibitors that are used to treat HIV, or the neuraminidase inhibitors developed to treat influenza, or the antiviral nucleoside analogues used to treat several types of virus, target specific viral proteins and enzymes. Viruses can rapidly develop mutations within their genomes that create variants of the drug targets which are no longer sensitive to inhibition by the drug. In contrast, squalamine creates an antiviral effect by inducing a state of resistance in the cells the virus is designed to target. No known genetic resistance mechanisms exist which a virus could acquire to overcome the inactivation of a fundamental cellular pathway required for cellular entry and infection.

III. Combination Therapy

The squalamine compositions and squalamine derivative compositions of the invention, may be administered alone or in combination with other therapeutic agents. For example, the squalamine or a derivative thereof may be administered in combination compounds including but not limited to, chemotherapeutic agents, antibiotics, steroidal and non-steroidal anti-inflammatories, conventional immunotherapeutic agents, and/or therapeutic treatments described below. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

A. Anti-Viral Agents

For example, squalamine compositions and squalamine analog compositions of the invention with conventional antiviral therapies for treating and preventing viral infections. For example, the squalamine and squalamine derivative compositions of the invention can be combined with any known antiviral agent.

Designing safe and effective antiviral drugs is difficult, because viruses use the host's cells to replicate. This makes it difficult to find targets for the drug that would interfere with the virus without harming the host organism's cells. Almost all anti-microbials, including anti-virals, are subject to drug resistance as the pathogens mutate over time, becoming less susceptible to the treatment. For instance, a recent study published in Nature Biotechnology emphasized the urgent need for augmentation of oseltamivir (Tamiflu®) stockpiles with additional antiviral drugs including zanamivir (Relenza®) based on an evaluation of the performance of these drugs in the scenario that the 2009 H1N1 'Swine Flu' neuraminidase (NA) were to acquire the Tamiflu®-resistance (His274Tyr) mutation which is currently wide-spread in seasonal H1N1 strains. Soundararajan et al., "Extrapolating from sequence—the 2009 H1N1 'swine' influenza virus". Nature Biotechnology 27 (6) (2009). Thus, there is a need for compositions, such as those described herein, which are useful in conjunction with conventional antiviral treatments.

Conventional antiviral treatments include, but are not limited to (1) Amantadine and rimantadine, which combat influenza and act on penetration/uncoating; (2) Pleconaril, which works against rhinoviruses, which cause the common cold; (3) nucleotide or nucleoside analogues, such as acyclovir, zidovudine (AZT), lamivudine; (4) drugs based on "antisense" molecules, such as fomivirsen; (5) ribozyme antivirals; (6) protease inhibitors; (7) assembly inhibitors, such as Rifampicin; (8) release phase inhibitors, such as zanamivir (Relenza) and oseltamivir (Tamiflu); (9) drugs which stimulate the immune system, such as interferons, which inhibit viral synthesis in infected cells (e.g., interferon alpha), and synthetic antibodies (A monoclonal drug is now being sold to help fight respiratory syncytial virus in babies, and antibodies purified from infected individuals are also used as a treatment for hepatitis B). Examples of antiviral drugs include, but are not limited to, Abacavir, Aciclovir, Acyclovir, Adefovir, Amantadine, Amprenavir, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Immunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Molixan (NOV-205), Moroxydine, Nelfinavir, Nevirapine, Nexavir, Nucleoside analogues, Oseltamivir (Tamiflu®), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Saquinavir, Stavudine, Synergistic enhancer (antiretroviral), Tenofovir, Tenofovir disoproxil, Tipranavir, Trifluridine, Trizivir, Tromantadine, Truvada, Valaciclovir (Valtrex®), Valganciclovir, Vicriviroc, Vidarabine, Viramidine, Zalcitabine, Zanamivir (Relenza®), and Zidovudine In certain embodiments, squalamine or a derivative thereof is administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the squalamine or a derivative thereof, include, but are not limited to, RETROVIR™ (zidovudine/AZT), VIDEX™ (didanosineIddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with squalamine composition, include, but are not limited to, VIRAMUNE™ (nevirapine), RESCRIPTOR™ (delavirdine), and SUSTIVA™ (efavirenz). Protease inhibitors that may be administered in combination with the squalamine or a derivative thereof include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with squalamine or a derivative thereof to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867 (Glaxo Wellcome); ZIAGEN™ (abacavir/159U89; Glaxo Wellcome Inc.); CS-87 (3' azido-2',3'-dideoxyuridine; WO 99/66936); and S-acyl-2-thioethyl (SATE)-bearing prodrug forms of beta-L-FD4C and β-L-FddC (WO 98/17281).

Additional NNRTIs include COACTINON™ (Emivirine/MKC442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myers Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756,423 (an indinavir analog; Merck); DMP450 (a cyclic urea compound; Avid & DuPont); AG-1776 (a peptidomimetic with in vitro activity against protease inhibitor-resistant viruses; Agouron); VX-175/GW433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX404C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine receptor agonists such as RANTES, SDF-1, MEP-1alpha, MIP-1beta, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compounds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors such as VX-497 (Vertex); and mycopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1alpha, MIP-1beta, SDF-1alpha, IL-2, PROLEUKIN™ (aldesleukin/L2-7001; Chiron), IL4, IL-10, IL-12, and IL-13; interferons such as IFN-alpha2a, IFN-alpha2b, or IFN-beta; antagonists of TNFs, NFkappaB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targeted to the ER to block surface expression of newly synthesized CCR5 (Yang et al., *PNAS,* 94:11567-72 (1997); Chen et al., *Nat. Med.,* 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-alpha antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and alpha-naphthoflavone (WO 98/30213); and antioxidants such as gamma-L-glutamyl-L-cysteine ethyl ester (gamma-GCE; WO 99/56764).

B. Anti-Inflammatory Agents

In certain embodiments, the squalamine or a derivative thereof is administered alone or in combination with an anti-inflammatory agent. Anti-inflammatory agents that may be administered with the squalamine or a derivative thereof include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

IV. Formulations

Compositions for pharmaceutical use typically comprise a pharmaceutically acceptable carrier, for example, solvents, dispersion media, coatings, isotonic and absorption delaying agents and the like, and combinations comprising one or more of the foregoing carriers as described, for instance, in REMINGTON'S PHARMACEUTICAL SCIENCES, 15th Ed. Easton: Mack Publishing Co. pp. 1405-1412 and 1461-1487 (1975), and THE NATIONAL FORMULARY XIV 14th Ed., Washington: American Pharmaceutical Association (1975). Suitable carriers include, but are not limited to, calcium carbonate, carboxymethylcellulose, cellulose, citric acid, dextrate, dextrose, ethyl alcohol, glucose, hydroxymethylcellulose, lactose, magnesium stearate, maltodextrin, mannitol, microcrystalline cellulose, oleate, polyethylene glycols, potassium diphosphate, potassium phosphate, saccharose, sodium diphosphate, sodium phosphate, sorbitol, starch, stearic acid and its salts, sucrose, talc, vegetable oils, water, and combinations comprising one or more of the foregoing carriers. The use of such media and agents for pharmaceutically active substances is well known in the art. Except insofar as any conventional media or agent is incompatible with the compositions of the present invention, their use in therapeutic compositions is contemplated. Supplementary active ingredients also can be incorporated into the compositions.

A. Pharmaceutical Carriers

While it is possible for a squalamine or a derivative thereof to be administered alone, it is preferable to present it as a pharmaceutical formulation, together with one or more acceptable carriers. The carrier(s) must be "acceptable" in the sense of being compatible with the squalamine or a derivative thereof and not deleterious to the recipients thereof. Typically, the carriers will be water or saline which will be sterile and pyrogen free. Squalamine or a derivative thereof is particularly well suited to formulation in aqueous carriers such as sterile pyrogen free water, saline or other isotonic solutions because of their extended shelf-life in solution. For instance, pharmaceutical compositions of the invention may be formulated well in advance in aqueous form, for instance, weeks or months or longer time periods before being dispensed.

Generally, the formulations are prepared by contacting the squalamine or a derivative thereof uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably comprises minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as gelatin, serum albumin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In instances where aerosol administration is appropriate, the squalamine or a derivative thereof can be formulated as aerosols using standard procedures. The term "aerosol" includes any gas-borne suspended phase of a squalamine or a derivative thereof which is capable of being inhaled into the bronchioles or nasal passages, and includes dry powder and aqueous aerosol, and pulmonary and nasal aerosols. Specifically, aerosol includes a gas-borne suspension of droplets of squalamine or a derivative thereof, as may be produced in a metered dose inhaler or nebulizer, or in a mist sprayer. Aerosol also includes a dry powder composition of a compound of the invention suspended in air or other carrier gas, which may be delivered by insufflation from an inhaler device, for example. See Ganderton & Jones, *Drug Delivery to the Respiratory Tract* (Ellis Horwood, 1987); Gonda, *Critical Reviews in therapeutic Drug Carrier Systems,* 6:273-313 (1990); and Raeburn et al., *Pharmacol. Toxicol. Methods,* 27:143-159 (1992).

B. Exemplary Dosage Forms

The formulations may conveniently be presented in unit dosage form and may be prepared by any of the methods well known in the art of pharmacy. Any pharmaceutically acceptable dosage form may be employed in the methods of the invention. A preferred dosage form is an orally administered dosage form, such as a tablet or capsule. Such methods include the step of bringing into association the squalamine or a derivative thereof with the carrier that constitutes one or more accessory ingredients. In general the formulations are prepared by uniformly and intimately bringing into association the active ingredient with liquid carriers or finely divided solid carriers or both, and then, if necessary, shaping the product.

1. Exemplary Dosage Forms

Formulations suitable for parenteral administration include aqueous and non-aqueous sterile injection solutions which may contain anti-oxidants, buffers, bacteriostats and solutes which render the formulation appropriate for the intended recipient; and aqueous and non-aqueous sterile suspensions which may include suspending agents and thickening agents. The formulations may be presented in unit-dose or multi-dose containers, for example sealed ampules, vials or syringes, and may be stored in a freeze-dried (Lyophilised) condition requiring only the addition of the sterile liquid carrier, for example water for injections, immediately prior to use. Extemporaneous injection solutions and suspensions may be prepared from sterile powders.

Formulations or compositions of the invention may be packaged together with, or included in a kit with, instructions or a package insert. For instance, such instructions or package inserts may address recommended storage conditions, such as time, temperature and light, taking into account the shelf-life of the squalamine or a derivative thereof. Such instructions or package inserts may also address the particular advantages of the squalamine or a derivative thereof, such as the ease of storage for formulations that may require use in the field, outside of controlled hospital, clinic or office conditions.

The squalamine or a derivative thereof can also be included in nutraceuticals. For instance, squalamine or a derivative thereof may be administered in natural products, including milk or milk product obtained from a transgenic mammal which expresses alpha-fetoprotein fusion protein. Such compositions can also include plant or plant products obtained from a transgenic plant which expresses the squalamine or a derivative thereof. The squalamine or a derivative thereof can also be provided in powder or tablet form, with or without other known additives, carriers, fillers and diluents. Exemplary nutraceuticals are described in Scott Hegenhart, *Food Product Design*, December 1993.

The invention also provides methods of treatment and/or prevention of diseases or disorders (such as, for example, any one or more of the diseases or disorders disclosed herein) by administration to a subject of an effective amount of a squalamine or a derivative thereof in a pharmaceutically acceptable carrier.

The squalamine or a derivative thereof will be formulated and dosed in a fashion consistent with good medical practice, taking into account the clinical condition of the individual patient (especially the side effects of treatment with the squalamine or a derivative thereof alone), the site of delivery, the method of administration, the scheduling of administration, and other factors known to practitioners. The "effective amount" for purposes herein is thus determined by such considerations.

As a general proposition, the total pharmaceutically effective amount of the squalamine or a derivative thereof administered parenterally per dose will be in the range of about 0.1 mg/kg/day to 20 mg/kg/day of patient body weight, although, as noted above, this will be subject to therapeutic discretion. An intravenous bag solution may also be employed. The length of treatment needed to observe changes and the interval following treatment for responses to occur appears to vary depending on the desired effect.

"Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous, transdermal, and intraarticular injection and infusion.

Squalamine or a derivative thereof is also suitably administered by sustained-release systems. Examples of sustained-release squalamine or a derivative thereof compositions are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion. Additional examples of sustained-release squalamine or a derivative thereof include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., *Biopolymers*, 22:547-556 (1983)), poly(2-hydroxyethyl methacrylate) (Langer et al., *J. Biomed. Mater. Res.*, 15:167-277 (1981), and Langer, *Chem. Tech.*, 12:98-105 (1982)), ethylene vinyl acetate (Langer et al., Id.) or poly-D-(−)-3-hydroxybutyric acid (EP 133,988).

Sustained-release squalamine or a derivative thereof also include liposomally entrapped squalamine or a derivative thereof (see generally, Langer, *Science*, 249:1527-1533 (1990); Treat et al., in *Liposomes in the Therapy of Infectious Disease and Cancer*, Lopez-Berestein and Fidler (eds.), pp. 317-327 and 353-365 (Liss, N.Y., 1989). Liposomes comprising the squalamine or a derivative thereof are prepared by methods known per se: DE 3,218,121; Epstein et al., *Proc. Natl. Acad. Sci.* (USA), 82:3688-3692 (1985); Hwang et al., Proc. Natl. Acad. Sci. (USA), 77:40304034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapeutic.

In yet an additional embodiment, the squalamine or a derivative thereof are delivered by way of a pump (see Langer, supra; Sefton, *CRC Crit. Ref Biomed. Eng.*, 14:201 (1987); Buchwald et al., *Surgery*, 88:507 (1980); Saudek et al., *N. Engl. J. Med.*, 321:574 (1989)).

Other controlled release systems are discussed in the review by Langer (*Science* 249:1527-1533 (1990)).

For parenteral administration, in one embodiment, the squalamine or a derivative thereof is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the therapeutic.

Any pharmaceutical used for therapeutic administration can be sterile. Sterility is readily accomplished by filtration through sterile filtration membranes (e.g., 0.2 micron membranes). Squalamine or a derivative thereof generally is placed into a container having a sterile access port, for example, an intravenous solution bag or vial having a stopper pierceable by a hypodermic injection needle.

Squalamine or a derivative thereof ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous squalamine or a derivative thereof solution, and the resulting mixture is lyophilized. The infusion solution is prepared by reconstituting the lyophilized squalamine or a derivative thereof using bacteriostatic Water-for-Injection.

The invention also provides a pharmaceutical pack or kit comprising one or more containers filled with one or more of the ingredients of the squalamine or a derivative thereof. Associated with such container(s) can be a notice in the form prescribed by a governmental agency regulating the manufacture, use or sale of pharmaceuticals or biological products, which notice reflects approval by the agency of manufacture, use or sale for human administration. In addition, the squalamine or a derivative thereof may be employed in conjunction with other therapeutic compounds.

2. Dosages

Examples of dosages of squalamine tolerated by humans are well known in the art. For example, Hao et al., (2003). "A Phase I and pharmacokinetic study of squalamine, an aminosterol angiogenesis inhibitor." Clin Cancer Res 9(7): 2465-71, describes exemplary dosages for a 5-day continuous i.v. infusion every 3 weeks for treating advanced solid malignancies. Dose levels ranging from 6 to 700 mg/m(2)/day. Hepatotoxicity, characterized by brief, asymptomatic elevations in transaminases and hyperbilirubinemia, was the principal dose-limiting toxicity of squalamine At 700 mg/m(2)/day, two of three patients developed grade 4 hyperbilirubinemia, which precluded further dose escalation. At 500 mg/m(2)/day, one of seven patients experienced dose-limiting grade 4 hyperbilirubinemia and grade 3 neurosensory changes, which resolved soon after treatment. Squalamine pharmacokinetics were dose-proportional. At 500 mg/m(2)/day, the mean (percentage coefficient of variation) clearance, half-life, and volume of distribution of squalamine were 2.67 liters/h/m(2) (85%), 9.46 h (81%), and 36.84 liters/m(2) (124%), respectively, and steady-state concentrations [20.08 micro g/ml (13%)] were well above those that inhibit angiogenesis in preclinical models. The study concluded that at a dose of 500 mg/m(2)/day, squalamine is well tolerated.

In addition, Herbst et al., (2003). "A phase I/IIA trial of continuous five-day infusion of squalamine lactate (MSI-1256F) plus carboplatin and paclitaxel in patients with advanced non-small cell lung cancer." Clin Cancer Res 9(11): 4108-15, also describes exemplary therapeutic dosage of squalamine. This reference describes a Phase I/IIA study designed to assess the safety, clinical response, and pharmacokinetics of squalamine when administered as a 5-day continuous infusion in conjunction with standard chemotherapy every 3 weeks in patients with stage IIIB (pleural effusion) or stage IV non-small cell lung cancer. Patients with chemotherapy-naive non-small cell lung cancer were treated with escalating doses of squalamine in combination with standard doses of paclitaxel and carboplatin. Paclitaxel and carboplatin were administered on day 1, followed by squalamine as a continuous infusion on days 1-5, every 21 days. The starting dose of squalamine was 100 mg/m(2)/day and escalated to 400 mg/m(2)/day; two of three patients at 400 mg/m(2)/day had dose-limiting toxicity that included grade 3/4 arthralgia, myalgia, and neutropenia. On the basis of safety and toxicity, 300 mg/m(2)/day was selected as the Phase II dose of squalamine in this combination regimen. The combination of squalamine given continuously daily for 5 days, with paclitaxel and carboplatin given on day 1, was well tolerated.

C. Adjuvants

The squalamine or a derivative thereof may be administered alone or in combination with adjuvants. An adjuvant is a substance that indirectly enhances the therapeutic activity of squalamine by stimulating the antiviral arm of the innate and/or the adaptive immune system. Adjuvants that may be administered with the squalamine or a derivative thereof include, but are not limited to, cytokines and/or interleukins (such as IL2, IL3, IL4, IL5, IL6, IL7, IL8, IL-9, IL10, IL-11, IL12, IL13, IL-14, IL15, IlL16, IL-17, IL-18, IL-19, IL-20, IL-21, anti-CD40, CD40L, IFN-gamma, TNF-alpha, IL-1alpha, IL-1beta), Lipid A, including monophosphoryl lipid A, bacterial products, endotoxins, cholesterol, fatty acids, aliphatic amines, paraffinic and vegetable oils, threonyl derivative, and muramyl dipeptide, alum, alum plus deoxycholate (ImmunoAg), MTP-PE (Biocine Corp.), QS21 (Genentech, Inc.), BCG (e.g., THERACYS®), MPL and nonviable preparations of *Corynebacterium parvum*. In a specific embodiment, squalamine or a derivative thereof is administered in combination with alum. In another specific embodiment, squalamine or a derivative thereof is administered in combination with QS-21. Further adjuvants that may be administered with the squalamine or a derivative thereof include, but are not limited to, Monophosphoryl lipid immunomodulator, AdjuVax 100a, QS-21, QS-18, CRL1005, Aluminum salts, MF-59, and Virosomal adjuvant technology.

D. Vaccines

Vaccines that may be administered with the squalamine or a derivative thereof include any antigen capable of eliciting an immune response. The vaccine may be comprised of either live or inactivated virus. Exemplary vaccines include, but are not limited to, vaccines directed toward protection against MMR (measles, mumps, rubella), polio, varicella, tetanus/diptheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, pertussis, PA-toxin (e.g., anthrax), Human Immunodeficiency Virus (HIV-1 and HIV-2), Avian Flu antigen (e.g., H5N1; avian influenza virus A/FPV/Rostock/34 (H7N1) (FPV)), cancer, Severe Acute Respiratory Syndrome (SARS), and tuberculosis. Useful antigens include but are not limited to viral, prion, bacterial, parasitic, mycotic, etc. antigens.

Combinations may be administered either concomitantly, e.g., as an admixture, separately but simultaneously or concurrently; or sequentially. In addition, as used herein "combination administration" includes compounds which are attached to the squalamine or a derivative thereof. This also includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

V. Methods of Treating and/or Preventing Viral Infections Using Squalamine Compositions The squalamine compositions and squalamine derivative compositions are particularly useful in decreasing the infectivity, morbidity, and/or rate of mortality associated with a variety of viruses.

The squalamine compositions described herein may be administered by any conventional method including parenteral (e.g. subcutaneous or intramuscular) injection or intravenous infusion, orally, rectally, parenterally, intracisternally, intravaginally, intraperitoneally, topically (as by powders, ointments, gels, drops or transdermal patch), otically, ocularly, bucally, pulmonarily (e.g., as an oral or nasal spray or as an aerosol dispersion). The treatment may consist of a single dose or a plurality of doses over a period of time. For example, in preferred embodiments the squalamine or squalamine derivative is administered parenterally (e.g. subcutaneously injection or intramuscularly injection) or intravenous infusion.

Squalamine has been administered intravenously through peripheral or central veins. Squalamine is widely distributed throughout all tissues including the brain. Squalamine exhibits many of the metabolic/clearance characteristics of a bile salt. When administered orally squalamine is almost fully captured by the liver and likely enters an enterohepatic cycle during its subsequent metabolism, suggesting that appropriate hepatic diseases could be treated by oral administration.

The methods and compositions may be formulated into a single or separate pharmaceutically acceptable syringeable composition. In this case, the container means may itself be an inhalant, syringe, pipette, eye dropper, or other like apparatus, from which the formulation may be applied to an infected area of the body, such as the lungs, injected into an animal, or even applied to and mixed with the other components of the kit.

The methods and compositions, or components of the methods and compositions can be formulated in a single formulation, or can be separated into binary formulations for later mixing during use, as may be desired for a particular application. Such components can advantageously be placed in kits for use against microbial infections, decontaminating instruments and the like. Such kits may contain all of the essential materials and reagents required for the delivery of the formulations to the site of their intended action as well as any desired instructions.

A. Viral Diseases

Squalamine or a derivative thereof can be used to treat or detect any known viral infectious agent, including but not limited to any viral agent described herein. Viruses are one example of an infectious agent that can cause disease or symptoms that can be treated or detected by squalamine or a derivative thereof. Examples of viruses, include, but are not limited to the following DNA and RNA viruses and viral families: "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picornaviridae (e g Rhinovirus, Poliovirus), Poxyiridae (such as Smallpox or Vaccinia), Potyviridae, Reoviridae (e.g., Rotavirus), Retroviridae (HTLV-I, HTLV-II, Lentivirus), Rhabdoviridae, Tectiviridae, and Togaviridae (e.g., Rubivirus). In one embodiment, the virus is herpes, pox, papilloma, corona, influenza, hepatitis, sendai, sindbis and vaccinia viruses, west nile, hanta, or viruses which cause the common cold. Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia.

Squalamine or a derivative thereof can be used to treat or detect any of these symptoms or diseases. In specific embodiments, squalamine or a derivative thereof is used to treat viral meningitis, Dengue, EBV, and/or hepatitis (e.g., hepatitis B). In an additional specific embodiment squalamine or a derivative thereof is used to treat patients nonresponsive to one or more other commercially available hepatitis therapies. In a further specific embodiment, squalamine or a derivative thereof is used to treat AIDS.

In another embodiment, squalamine or a derivative thereof is used to treat a chronic disease suspected to be of viral origin. These conditions include diseases such as multiple sclerosis, Type I and Type II diabetes, atherosclerosis, cardiomyopathies, Kawaski disease, aplastic anemia, and so on.

EXAMPLES

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

Example 1

This example demonstrates the capacity of squalamine to displace proteins associated with the inner surface of the plasma membrane through electrostatic interactions.

The basic methods utilized in this example are described in the published literature (Yeung, Terebiznik et al. 2006; Yeung, Gilbert et al. 2008). The methodology described in these published reports provide tools to measure the electrostatic potential of the inner surface of the cell membrane, that being the side faces the cytoplasm of a cell. The published method comprises introducing into a cell a fluorescent protein that contains a strong cationic (positively charged) region. This fluorescent protein, because of its strong positive charge will bind to negatively charged membranes, causing the membrane to "light up" as a consequence of the attachment to it of the fluorescent probe. Should the strong negative charge on the plasma membrane be lost, for example, due to hydrolysis of the phosphatidyl serine, the fluorescent probe would fall off and diffuse into the cytoplasm. Thus the segregation of the fluorescent signal on the membrane indicates the persistence of the available negative charge of the cytoplasmic face of the membrane. In general, these probes are comprised of a standard fluorescent protein (like green fluorescent protein) to which a short peptide is fused corresponding to the cationic region of proteins that anchor to the cytoplasmic face of the plasma membrane. The tools and methods described in the literature and used in this example have demonstrated that electrostatic interactions between the negatively charged inner surface of the cytoplasmic surface of the plasma membrane and the cationic regions anchor many members of the Ras/Rho small GTPases to their membrane locus and confirm that the anionic phospholipids on the inner face of the plasma membrane create a strong, negatively charged surface. (Yeung, Terebiznik et al. 2006; Yeung, Gilbert et al. 2008).

A RAW 264.7 macrophage line was transfected with engineered recombinant vectors to generate cells that expressed two peptide probes, each linked to a red or green fluorescent protein to permit microscopic visualization. "Trunc Cat Tail" (GFP-ARDGRRRRRRARARCVIM) is a highly cationic probe. "H-Ras" (RFP—full length H-Ras) is a member of the Ras family of proteins that associates with the plasma membrane principally through interactions dominated by two fatty acid chains covalently attached to the carboxyterminal end of the molecule. This binding interaction depends principally on hydrophobic interactions ("oil prefers to mix with oil over water") rather than through electrostatic (charge based) interactions. Prior to exposure of these cells to squalamine, both H-Ras and Trunc Cat Tail can be seen associated with the plasma membrane (FIG. 2, upper set of panels). Following the addition of squalamine (10 micromolar) to the culture medium in which the cells are bathed, the True Cat Tail probe is displaced into the cytoplasm, while the H-Ras probe remains associated with the membrane.

Results: Since the H-Ras probe has not been displaced, it can be concluded that squalamine did not disrupt the physical integrity of the membrane, and cause widespread detachment of all associated proteins. The release of the Trunc Cat Tail probe strongly suggests that squalamine has reduced the net negative electrostatic potential, resulting in release of the cationic probe from the plasma membrane, its entry into the cytoplasm, and relocation to favorable anchoring sites on various intracellular membranes.

Example 2

In this experiment, the results of which have been published (Yeung, Gilbert et al. 2008), the RAW264.7 cell line has been engineered to express a red tagged fluorescent protein ("Lact-C2") that binds avidly to phosphatidylserine through forces that are not based solely on electrostatic potential. In addition the cell also expresses a green tagged fluorescent cationic fragment ("R-pre"), similar in sequence and design to the "Trunc Cat Tail" probe discussed above.

As seen in FIG. 3, before addition of squalamine, both probes are seen to be associated with the plasma membrane, as expected. In addition to its localization at the plasma membrane, the Lact-C2 probe can be seen decorating intracellular membranes as well, reflecting the sites within the cell that are rich in phosphatidylserine (Yeung, Gilbert et al. 2008). The restricted localization of R-pre to the plasma membrane reflects the highly cationic charge on R-pre (8 positive charges) and the fact that the cytoplasmic surface of the plasma membrane exhibits the strongest negative electrostatic potential of any major membrane in an animal cell (Yeung, Gilbert et al. 2008).

Within several minutes following exposure of these cells to squalamine (80 μM, 30 minutes), R-pre was displaced from its residence on the plasma membrane to other areas within the cell's interior. In contrast, exposure of these cells to squalamine did not alter the localization of Lact-C2.

This example demonstrates that squalamine reduces the electrostatic potential of the membrane into which it sits, displacing proteins bound via "non-specific" electrostatic forces, but cannot necessarily displace a protein that binds to phosphatidylserine through forces based on chemically specific features of that lipid.

Example 3

This example determines whether squalamine is a substrate for the organic cation transporter (Oct). This determination employed a standard transport competition assay, described in the literature (Lips, Volk et al. 2005).

Chinese hamster ovary cells, previously engineered to over-express a specific human Oct transporter were used in the assay. In this example, the effect of a specific concentration of an aminosterol is determined on the intracellular uptake of radiolabelled 1-methyl-4-phenylpyridine (MPP) (at 0.01 μM), measured after a 1-second exposure. The extent to which the added compound inhibits the uptake is recorded (as % inhibition). $IC_{50}$ refers to the concentration of squalamine or 1436 required to inhibit MPP uptake by 50%. Table 1 below describes the affinity of squalamine and Aminosterol 1436 for human organic cation transporters (Human Oct 1, Human Oct 2, and Human Oct 3) based upon the MPP uptake inhibition assay.

TABLE 1

Affinity of Squalamine and 1436 for the human organic cation transporters based on an MPP uptake inhibition assay

| Transporter | % Inhibition of MPP uptake caused by 100 μM Squalamine (IC50) | % Inhibition of MPP uptake caused by 100 μM 1436 (IC50) |
|---|---|---|
| Human Oct 1 | 25% (34 μM) | 0 (up to 1 mM 1436) |
| Human Oct 2 | 40% (50 μM) | 0 (up to 1 mM 1436) |
| Human Oct 3 | 60% (83 μM, 16 μM) | 70% (29 μM, 34 μM) |

The values obtained for squalamine and Aminosterol 1436 compare in magnitude with substances previously described in the literature and already known to be transported via Oct proteins (Koepsell 2004).

Thus, the results of this example demonstrate that squalamine is a substrate for the known Oct1 3 transporters, suggesting that squalamine has a greater opportunity for entering all tissues and organs of the body, since one or another of these transporters in universally expressed. For example, squalamine should be capable of entering brain microvascular capillaries, since Oct 2 is known to be expressed in those cells (Sung, Yu et al. 2005). In contrast, Aminosterol 1436 is recognized solely by Oct 3, which is most abundantly expressed in placenta and heart, and the least abundantly expressed of the transporters. Thus, this Example predicts that squalamine should readily accumulate within endothelial cells, while Aminosterol 1436 should not, which is indeed the case (as shown in Example 4).

Example 4

The purpose of this example was to determine the kinetics of squalamine and Aminosterol 1436 update into endothelial cells.

Human umbilical endothelial cells were grown as described (Sills, Williams et al. 1998). Flasks containing cells at 75% confluence were incubated with $^3$H squalamine or $^3$H-1436 (2 uCi/ml, 1 µg/ml) in 5 ml fresh medium. After various times the medium was removed, washed with PBS and cells released by scrapping. The cells were counted, and then collected by brief centrifugation, followed by resuspension in 1 ml of buffer containing 10 mM Tris-HCl, 2 mM $CaCl_2$, 1 mM Mg $Cl_2$, 1 mM DTT, and lysing with 10 strokes of a loose fitting Dounce homogenizer. Radioactivity contained in aliquots of the homogenates was measured by scintillation counting. The results are shown in Table 2, below.

TABLE 2

Kinetics of uptake of squalamine and Aminosterol 1436 into endothelial cells

| Time (min) | Molecules/cell ($\times 10^{-6}$) | |
|---|---|---|
| | Squalamine | Aminosterol 1436 |
| 5 | 250 | 2 |
| 30 | 400 | |
| 60 | 500 | 3 |
| 120 | 500 | |
| 180 | 600 | 2 |

This example demonstrates that the entry of squalamine into the HUVEC is over 2 orders of magnitude greater than for Aminosterol 1436, reflecting the difference in transporter affinities expressed by the endothelial cell specific for the two aminosterols. Aminosterol 1436 cannot enter the endothelial cell because this cell type does not express Oct 3, the sole transporter currently known to permit Aminosterol 1436 to gain entry into the membrane; squalamine, in contrast, can readily enter through Oct 1 and Oct 2, both of which are known to be expressed in endothelial cells.

As reported below, Aminosterol 1436 does not appear to functionally neutralize the electrostatic potential of the plasma membrane of the endothelial cell, best understood as a consequence of the failure of the compound to enter this cell type.

Example 5

This example is directed to using a screening method to identify analogs of squalamine that exhibit in vitro properties comparable to squalamine on the dynamics of the actin cytoskeleton in the endothelial cell.

The basic methods have been published (Williams, Weitman et al. 2001). HUVECs were grown on fibronectin-covered coverslips in EGM medium. The cells were then incubated in the presence of thrombin (20 ng/ml), and either the aminosterol (20 µM), or an equivalent volume of water, for 2 hours. The treated cells were fixed with 3.7% formaldehyde, permeabilized with 0.1% Triton X-100, and incubated with a 1:100 dilution of murine anti-VE-cadherin monoclonal antibody. Following a rinse, the cells were exposed to a 1:400 dilution of an FITC-goat antimurine antibody and 250 ng/ml TRITC phalloidin. The stained coverslips were visualized by fluorescence microscopy.

The aminosterols evaluated were squalamine and several analogs, the structures of which are presented in Table 3. The results of the assay are summarized in Table 4.

TABLE 3

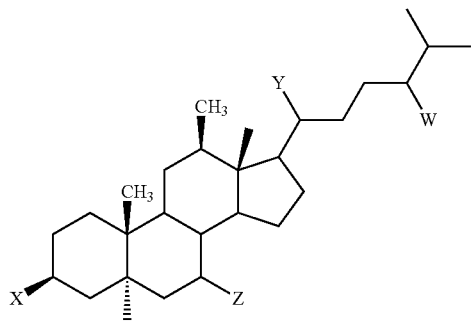

| Compound | Structure |
|---|---|
| Squalamine | X = 3β-$H_2$N—($CH_2$)$_4$—NH—($CH_2$)$_3$—NH—, Z = 7α-OH, Y = 20R—$CH_3$, W = 24R-sulfate |
| A | X = 3β-$H_2$N—($CH_2$)$_4$—NH—($CH_2$)$_3$—NH—, Z = 7β-OH, Y = 20R—$CH_3$, W = 24R-sulfate |
| B | X = 3α-$H_2$N—($CH_2$)$_4$—NH—($CH_2$)$_3$—NH—, Z = 7α-OH, Y = 20R—$CH_3$, W = 24R-sulfate |
| C | X = 3β-$H_2$N—($CH_2$)$_4$—NH—($CH_2$)$_3$—NH—, Z = 7α-OH, Y = 20R—$CH_3$, W = 24S-sulfate |
| D | X = 3β-$H_2$N—($CH_2$)$_4$—NH—($CH_2$)$_3$—NH—, Z = 7α-OH,, Y = 20S—$CH_3$, W = 24R-sulfate |
| E | X = 3-$NH_3$, Z = 7α-OH, Y = 20R—$CH_3$, W = 24R-sulfate |
| F | X = 3β-$H_2$N—($CH_2$)$_3$—O—($CH_2$)$_3$—NH—, Z = 7α-OH, Y = 20R—$CH_3$, W = 24R-sulfate |
| G (Aminosterol 1436) | X = 3β-spermine, Z = 7α-OH, Y = 20R—$CH_3$, W = 24R-sulfate |

TABLE 4

| Aminosterol | Disruption of thrombin induced stress fiber formation |
|---|---|
| Squalamine | Yes |
| A | Yes |
| B | Yes |
| C | Yes |
| D | No |
| E | No |
| F | No |
| G | No |

As seen in Table 4, certain stereo-isomers of squalamine, such as the 3-α isomer, the 24 S isomer, and the 7β hydroxy isomer, each inhibited thrombin-induced stress fiber formation. In contrast, aminosterols D-G were inactive. Compound D, a stereoisomer of squalamine, differs from squalamine at a single stereo-center ($C_{20}$). Compound E, differs from squalamine by having a single amino group fixed to 3C instead of a spermidine; Compound F differs from squalamine by having a spermidine-like moiety that carries only 2 positive charges instead of the 3 carried by spermidine; and G is Aminosterol 1436, identical to squalamine, expect for the presence of a spermine moiety (4 charges) in place of a spermidine (3 charges) at C3.

The results of this Example demonstrate that only certain isomers of squalamine can enter cells, reduce electrostatic potential, and disturb actin cytoskeletal dynamics. These data highlight the highly specific structural constraints that must be met by active squalamine analogues, and must reflect the highly specific nature of the molecular interactions responsible for the biological effect being observed.

The antiviral properties of squalamine disclosed herein are believed to depend on the ability of the aminosterol to both enter cells and also neutralize the negative electrostatic potential of the inner surface of the plasma membrane to a degree that causes release of proteins anchored electrostatically to the plasma membrane. Hence, only those compounds that can inhibit growth-factor induced stress fiber formation as monitored in the in vitro assay above, would be expected to exhibit antiviral via the mechanism proposed for squalamine.

Example 6

The purpose of this example was to demonstrate the effectiveness of squalamine in treating a viral infection, such as Yellow Fever. The results show that squalamine can effectively prevent Yellow Fever infection in inoculated hamsters.

The hamster is used as an animal model to study yellow fever because it develops a disease following infection with the Yellow fever virus that resembles the human Yellow Fever infection. Yellow fever is a member of the Flaviviridae, which includes Hepatitis C, Dengue Fever Virus, Japanese Encephalitis Virus, Tick Borne Encephalitis Virus, Bovine Viral Diarrheal Virus, Classical Swine Fever Virus, Border Disease Virus, and Hepatitis G virus (Leyssen, De Clercq et al. 2000). To date, only a limited number of substances have proven effective in this model. They include antiviral nucleoside analogs such as ribavirin and interferon-alpha (Sbrana, Xiao et al. 2004).

The experimental model used in this example has been published in detail (Tesh, Guzman et al. 2001; Xiao, Zhang et al. 2001) and used in the evaluation of antiviral therapeutics ((Sbrana, Xiao et al. 2004).

Study Design:

The study design for this Example is given in Table 5, below.

TABLE 5

Study Design

| Parameter | |
|---|---|
| Virus | Jimenez hamster-adapted yellow fever virus inoculated intraperitoneal (i.p.) |
| Number of animals | 10/group 20/placebo group |
| Treatment route | intraperitoneal (i.p.) |
| Start of Treatment | −24 hours |
| Treatment times | daily for 8 days (−24 h to 6 days post-virus inoculation (dpi)) |
| Parameters | Percent survivors, serum ALT/AST levels determined on day 6, mean day to death, weight change between 3 and 6 dpi |
| Infected Groups | Group 1- Squalamine 7.7 mg/kg/d, qd Group 3- Squalamine 2.5 mg/kg/d, qd Group 5- Squalamine 0.7 mg/kg/d, qd Group 7- Ribavirin 50 mg/kg/d, bid Group 9- Saline |

Results: As seen in FIG. 4, survival increased in response to increasing doses of squalamine At 7.7 mg/kg, administered as a single daily dose, the survival fraction of the squalamine treated group was nearly identical to the group that received ribavirin (50 mg/kg/day). (Note: "bid" in Table 5 refers to twice a day dosing, while "qd" refers to once a day dosing.)

These results demonstrate the effectiveness of squalamine as an antiviral agent.

Example 7

The purpose of this example was to evaluate the effectiveness of squalamine in treating a viral infection, such as Yellow Fever, when administered subcutaneously, in a head-to-head comparison with ribavirin, over a comparable dosing schedule. Ribavirin is a nucleoside analogue that is effective in the hamster model when administered via an optimized dosing schedule. Ribavirin is used as an antiviral therapeutic in humans, mainly for the treatment of Hepatitis C, in conjunction with Interferon-α.

Experimental Design:

Hamsters were randomly assigned to groups, with 10 included in each and 20 placebo-treated controls. A $10^{-4}$ dilution ($10^{2.0}$ $CCID_{50}$/ml) of the virus was prepared in minimal essential media. Hamsters were injected intraperitoneally (i.p.) with 0.1 ml of the diluted virus (10 $CCID_{50}$/animal). Squalamine was administered subcutaneously (s.c.) at a total daily dose 15 mg/kg/d, given once a day (qd) beginning 24 h before introduction of virus and ending on 6 days post infection(dpi). Ribavirin was administered intraperitonealy (i.p.) at doses of 3.2, 10, or 32 mg/kg/d administered once daily beginning 24 h before introduction of virus and ending on 6 days post infection (dpi). Mortality was observed daily for 21 days, and weight was recorded on 0, 3, and 6 dpi.

Statistical Analysis:

Survival data were analyzed using the Wilcoxon log-rank survival analysis and all other statistical analyses were done using one-way ANOVA using a Bonferroni group comparison (Prism 5, GraphPad Software, Inc).

Figure 5:
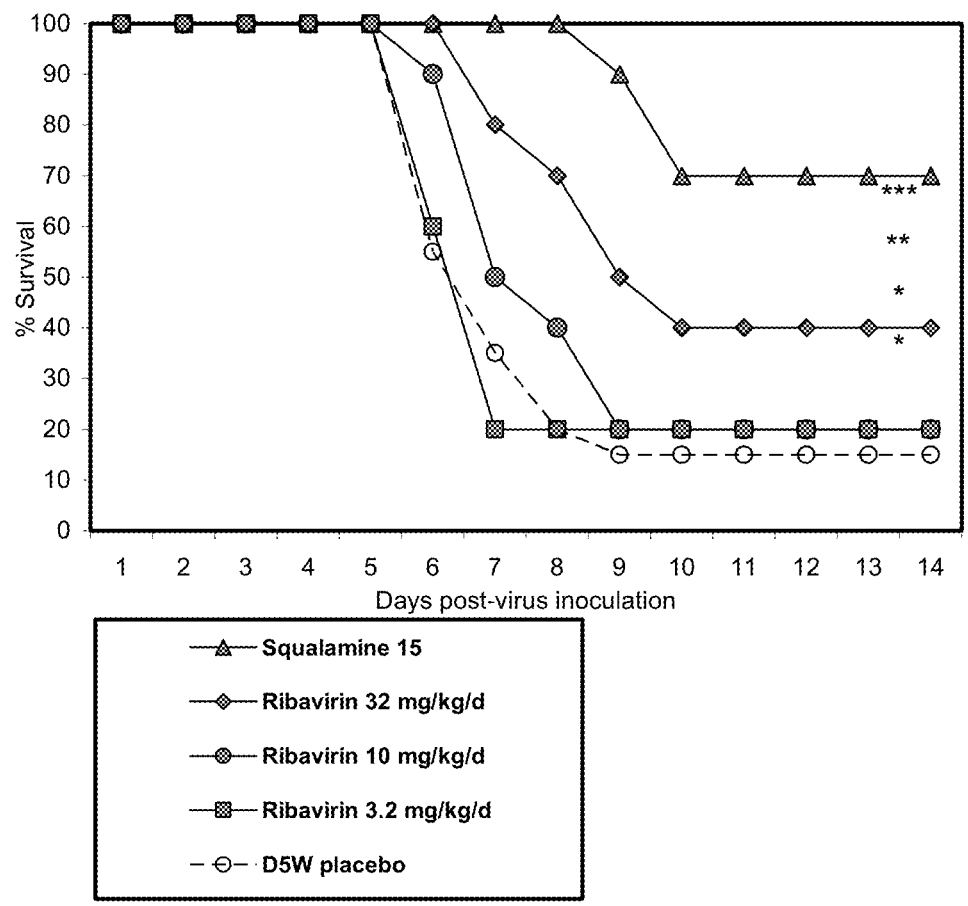
FIG. 5: Shows the results of an in vivo test to determine the effectiveness of squalamine against Yellow Fever in Syrian hamsters in a head-to-head comparison with the antiviral drug ribavirin. Squalamine at 15 mg/kg was administered subcutaneously daily, while ribavirin was administered once daily i.p. at either 3.2, 10, and 32 mg/kg. Squalamine was the most effective treatment, with 70% of the animals surviving, compared with about 10% of those receiving vehicle. Ribavirin was less effective, the maximal dose achieving a survival of 40%.

Results:

Treatment with squalamine resulted in 70% survival compared with 15% of animals receiving vehicle alone (FIG. 5). About 40% of the animals receiving ribavirin at the highest dose (32 mg/kg/day) survived, while those receiving lower doses fared no better than the placebo-treated cohort.

These results illustrate the effectiveness of squalamine as an antiviral agent and demonstrate that its antiviral activity in an animal is comparable to a well-studied antiviral agent currently in use as a human therapeutic drug against another flavivirus, Hepatitis C.

Example 8

The purpose of this experiment was to evaluate the efficacy of systemically administered squalamine as an antiviral treatment in a setting where the viral infection, such as Yellow Fever, has already been established.

Experimental Design:

Hamsters were randomly assigned to groups, with 10 included in each and 20 placebo-treated controls. A $10^{-4}$ dilution ($10^{2.0}$ $CCID_{50}$/ml) of the virus was prepared in minimal essential media. Hamsters were injected into the peritoneum (i.p.) with 0.1 ml of the diluted virus (10 $CCID_{50}$/animal). Squalamine was administered subcutaneously (s.c.) at a total daily dose 15 mg/kg/d, given once a day (qd) beginning 24 h after introduction of virus and ending on 8 days post infection(dpi), 30 mg/kg/d, given once a day (qd) beginning 24 h after introduction of virus and ending on 8 days post infection(dpi), and 30 mg/kg/d, given once a day (qd) beginning 48 h after introduction of virus and ending on 9 days post infection(dpi). Mortality was observed daily for 21 days, and weight was recorded on 0, 3, and 6 dpi.

Statistical Analysis: Survival data were analyzed using the Wilcoxon log-rank survival analysis and all other statistical analyses were done using one-way ANOVA using a Bonferroni group comparison (Prism 5, GraphPad Software, Inc).

Results:

(FIG. 6) Whereas 100% of animals untreated died of Yellow Fever by day 11 post-infection, 60% of animals treated at 1 dpi with 15 mg/kg/day (s.c.) squalamine for 8 days survived and appeared to be cured as measured by continued survival through day 21. Similarly, 60% of animals treated at 1 dpi with 30 mg/kg/day appeared to have been cured as indicated by survival through day 21. Treatment remained effective even when dosing began on 2 dpi, with 40% of animals cured, when treated with squalamine at 30 mg/kg/day (s.c.) for 9 days.

The results of this example demonstrate that squalamine can be utilized as an effective systemic antiviral therapy in already established viral infection. Because of the similarity in the properties shared by the flavivirus family, in addition to Yellow Fever, squalamine could be used to treat infections caused other members of the Flaviviridae including: Dengue, Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

Yellow fever virus utilizes a pH dependent entry pathway to initiate infection. Based on the mechanism of action of squalamine and the efficacy of squalamine in the treatment of an established infection caused by Yellow fever, squalamine could be considered for the treatment of other infections caused by viruses that utilize a pH dependent entry pathway such as members of the Orthomyxoviridae including: Influenza A, B, C, Isavirus, Thogotovirus; members of the Rhabdomyoviridae, including: Vesiculovirus, Lyssavirus, Cytorhabdovirus, Nucleorhabdovirus, Novirhabdovirus; members of the Adenoviridae including: all Human Adenovirus types (1-55) and species (A-G), Atadenovirus, Avidenovirus, Icthadenovirus, Mastadenovirus, Siadenovirus; members of the Parvoviridae; members of the Filoviridae; members of the Iridoviridae; the Rubella virus.

Example 9

The purpose of this experiment was to evaluate the efficacy in an animal of systemically administered squalamine against a DNA virus. In this example mice have been infected with murine cytomegalovirus (MCMV), a virus similar to CMV that infects humans.

Experimental Design:

In this experiment mice were treated 24 hours prior to infection and treatment continued daily for 6 days post infection. Animals were sacrificed on days 3, 7, and 14, organs were harvested, and virus content determined by a standard viral plaque assay. 54 male Balb/c mice were inoculated into the peritoneum (i.p.) with 0.1 ml of a virulent strain of MCMV following a published protocol (Cavanaugh, Deng et al. 2003). 18 animals received 5% dextrose i.p., and served as controls; 18 received 10 mg/kg/day of squalamine i.p., as a 1 mg/ml solution in 5% dextrose; 18 received 10 mg/kg/day of squalamine s.c. On days 3, 7, and 14, 6 animals from each dosing cohort were randomly selected, euthanized and viral titers determined from the liver, spleen, lung, and submaxillary gland.

Statistical Analysis: Statistical analyses were done using one-way ANOVA using a Bonferroni group comparison or via Student's T test (Prism 5, GraphPad Software, Inc.).

Results: (FIG. 7) At day 3 a greater than 10-fold reduction in viral growth was observed in liver, spleen, and lung in animals that had received squalamine via the i.p. route, with little effect observed in the salivary gland. Between day 3 and 7, viral titers in spleen and liver fell about 10-fold in all groups, with the viral titers in the s.c. and i.p. groups significantly lower than in the control cohort; in contrast, viral titers increased between days 3 and 7 in the lungs and salivary glands, with no significant differences observed between groups. By day 14, 8 days after squalamine had stopped, virus was undetectable in the liver and spleen of animals that had received squalamine i.p., and was significantly reduced in the s.c. treatment group compared with controls. A trend toward reduction in viral titers in lung compared with control was observed in the i.p. treatment group.

The results of this example demonstrate that squalamine systemically administered to an animal can effectively treat CMV infection and reduce viral titers to undetectable levels. Hence, squalamine can exhibit antiviral activity systemically against both RNA and DNA viruses.

This experiment also demonstrates that squalamine is active against a member of the Herpes Virus family, and supports its use in infections caused by other members of the Herpes family, including Human cytomegalovirus, Herpes Simplex 1, Herpes Simplex 2, Epstein Barr Virus, Varicella Zoster Virus, Roseolovirus (HHV6 and HHV7), Kaposi's Sarcoma Associated Herpes Virus, Cercopithecine herpesvirus-1, Murine gammaherpesvirus-68, the Bovine Herpesviridae, the Canine Herpesviridae, the Equine Herpesviridae, the Feline Herpesviridae, the Duck Herpesviridae, the Chicken Herpesviridae, the Turkey Herpesviridae, Porcine Herpesviridae and any as yet undiscovered virus subsequently classified as a member of the Herpesviridae.

This experiment also demonstrates, by virtue of the measured reduction in viral titers within the spleen, that squalamine administered systemically can effectively render virally resistant the cells of the spleen that support CMV infection, which include macrophages. This result supports the use of squalamine in the treatment of all viral diseases in which the macrophage is subject to infection.

Example 10

The purpose of this experiment was to evaluate the efficacy of systemically administered squalamine against the Eastern Equine Encephalitis Virus, an RNA virus of the alphavirus family.

Experimental Design: In this experiment hamsters (Syrian golden) were treated with either 5% dextrose (n=10, each species) or 10 mg/kg/day s.c. squalamine (n=10), beginning 24 hours prior to infection with EEEV, administered s.c., following a published protocol (Paessler, Aguilar et al. 2004). Treatments continued for 6 days after infection. Plasma viral titers were measured, along with body weights and survival.

Statistical Analysis: Survival data were analyzed using the Wilcoxon log-rank survival analysis and all other statistical analyses were done using one-way ANOVA using a Bonferroni group comparison, or via Student's T test (Prism 5, GraphPad Software, Inc).

Results: Squalamine administration extended survival in the hamster cohort (FIG. 8). At the end of treatment, 6/10 hamsters receiving squalamine were still alive, compared with 0/10 receiving vehicle. Concentration in the bloodstream of the hamster were determined (the mice were not studied since squalamine was ineffective). Plasma concentrations of virus were lower by about 100 fold in hamsters that had received squalamine compared with vehicle over the first 3 days post infection, confirming that squalamine has antiviral activity in an animal, likely the cause of improved survival (FIG. 9). We assume that a more pronounced effect on viremia would be observed with administration of higher squalamine doses.

The results of this example demonstrate that squalamine can effectively reduce the concentration of virus in an animal when administered systemically. This experiment also demonstrates the activity of squalamine in treating an infection caused by a member of the Alphavirus family and supports its use in the treatment infection caused by other members of this family, including: Aura virus, Barmah Forest virus, Bebaru virus, Cabassou virus, Chikungunya virus, Eastern equine encephalitis virus, Everglades virus, Fort Morgan virus, Getah virus, Highlands J virus Mayaro virus, Middelburg virus, Mosso das Pedras virus (78V3531, Mucambo virus, Ndumu virus, O'nyong-nyong virus, Pixuna virus, Rio Negro virus, Ross River virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus, Whataroa virus, as well as any as yet undiscovered virus subsequently classified as a member of the Alpaviridae.

Example 11

The purpose of this experiment was to demonstrate the antiviral effects of squalamine against Dengue. Dengue is a flavivirus, related to Yellow Fever Virus, and human Hepatitis C virus. The study was conducted in cell culture and utilized as substrate for infection a well studied line of human endothelial cells (HMEC-1) anticipated to be responsive to squalamine based on squalamine's known activity against endothelial cells.

Experimental Design: Cells were grown on uncoated glass cover-slips following a published protocol (Zamudio-Meza, Castillo-Alvarez et al. 2009). The cells were pretreated with squalamine for 2 hr at 37° C. prior to viral exposure; virus (multiplicity of infection of 3) remained in contact with cells for 30 minutes at 4° C., followed by 90 minutes at 37° C. The medium was then replaced with fresh medium lacking virus and squalamine and maintained at 37° C. for 48 hrs. Cells were fixed and processed for immunohistochemical detection of viral E protein. Viral E protein expression was used to monitor the early stages of infection.

Results: Viral infection was markedly diminished at concentrations of about 40 µg/ml (80%), with almost 100% inhibition at 60 µg/ml and higher (FIG. 10). Cell viability was not diminished at the effective squalamine concentrations, based on morphology and appearance under phase contrast.

This experiment demonstrates that squalamine has direct antiviral activity against Dengue, a non-enveloped RNA virus of the flavivirus family. Because of the similarity in the properties shared by the flavivirus family, in addition to Yellow Fever and Dengue, squalamine would be expected to be active against Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

Example 12

The purpose of this experiment was to determine the antiviral activity of squalamine against human Hepatitis B virus. The experiment was conducted in vitro, using primary human hepatocytes.

Experimental Design: Primary human hepatocytes were established in a 96 well microtiter plate. Squalamine was then added at concentrations of 2, 6 or 20 µg/ml followed by an inoculum of Hep B virus, and then in culture for 16 hours, after which fresh medium was introduced, and the cells maintained in culture for 14 days. In a second experiment, squalamine at 6 or 20 µg/ml was added to the cells at 24 hours post inoculation for a 16 hour exposure, followed by removal of medium, replacement with fresh medium, and continued culture for 14 days. Viral growth was measured by PCR using viral specific primers and normalized to the total RNA extracted from each corresponding well.

Results: Squalamine effectively inhibited HepB viral replication in human primary hepatocytes when added either during the initial exposure of virus to the cells, or at 24 hours. At a concentration of 20 µg/ml squalamine inhibited viral production by 83% when added during initial stages of infection, and by 64% when added at 24 hours; at a concentration of 6 µg/ml squalamine inhibited viral production by 54% when added at the onset of infection, and by 30% when added at 24 hours; squalamine at 2 µg/ml, added only at the outset of infection, inhibited production by 14%.

The experiment demonstrates that squalamine can exert antiviral activity against a human Hepatitis B virus infection of human liver. The experiment demonstrates that squalamine can inhibit the early phase of infection as well as the production of virus of cells already infected. These data support the use of squalamine for the treatment of acute and chronic viral hepatitis caused by Hepatitis B.

Example 13

The purpose of this experiment was to determine the antiviral activity of squalamine against human Hepatitis Delta virus. HDV is a small circular RNA virus that causes hepatitis by itself or in conjunction with Hepatitis B virus. The experiment was conducted in vitro, using primary human hepatocytes.

Experimental Design: Primary human hepatocytes were established in a 96 well microtiter plate. Squalamine was then added at concentrations of 20 or 60 µg/ml followed by an inoculum of Hep D virus, and then in culture for 3 hours, after which fresh medium was introduced, and the cells maintained in culture for 7 days. Viral growth was measured by PCR using viral specific primers and normalized to the total RNA extracted from each corresponding well.

Results: Squalamine effectively inhibited Hepatitis Delta viral replication in human primary hepatocytes when added during the initial exposure of virus to the cells. At a concentration of 20 µg/ml squalamine inhibited viral production by 90% when added during initial stages of infection. The 60 µg/ml concentration proved to be cytotoxic in vitro.

The experiment demonstrates that squalamine can exert antiviral activity against a human Hepatitis Delta virus infection of human liver. These data support the use of squalamine for the treatment of acute and chronic viral hepatitis caused by Hepatitis Delta virus. Since Hepatitis B and D frequently co-infect the same individual, these data would support use of squalamine for the treatment of both infections concurrently.

Squalamine inhibits the replication of both Hepatitis B virus and Hepatitis D virus in primary human hepatocytes, two viruses that differ in their structure, mode of entry, and replicative biology, a result anticipated by the proposed antiviral mechanism of squalamine. These results strongly suggest that squalamine should be effective against other viral infections of the human liver caused by the common Hepatitis viruses: Hepatitis A virus, Hepatitis E, Hepatitis F and Hepatitis G, and any other viral infection of the hepatocyte.

Example 14

The purpose of this experiment was to determine the antiviral activity of squalamine against human immunodeficiency virus (HIV).

Experimental Design: A line of HeLa cells is utilized that expresses the receptors and co-receptors required for the binding and entry of HIV, namely CXCR4, CD4 and CCR5. The HeLa line also has a luciferase reporter gene driven by the HIV-LTR so if infection occurs luciferase is expressed (Harmon, Campbell et al.). The amount of luciferase made is measured and serves as a measure of infection. The cells are plated and infected in the presence or absence of the squalamine A strain of vesicular stomatitis virus (VSV) that contains HIV genes required to activate the luciferase gene is utilized as a toxicity control, and should infect the cells equally well with or without the squalamine (unless squalamine also inhibits the infectivity of VSV). Once the cells are infected they incubate for at least 1 day (in the presence of the drug). The virus and drug are removed from the cells and then the cells are lysed with PBS+0.2% TritonX-100. Luciferase assays are done on the lysates to measure the level of infection.

Results: Squalamine inhibited HIV infection by about 50% at a concentration of 30 µg/ml compared with vehicle alone, with no evidence of toxicity apparent. At 20 µg/ml inhibition of about 20% was observed.

These data support the use of squalamine for the treatment of HIV and other retroviral infections. In addition these data demonstrate that squalamine can block the infectivity of enveloped viruses that enter cells via a pH independent fusion process. Thus, these data support the use of squalamine in the treatment of viral infections caused by viruses such as the retroviridae and the paramyxoviridae, including: Newcastle disease virus, Hendravirus, Nipah virus, measles virus, Rinderpest virus, Canine distemper virus, Sendai virus, Human parainfluenza 1, 2, 3, 4, mumps virus, Menangle virus, Tioman virus, Tuhokovirus 1,2,3, Human respiratory syncytial virus, avian pneumovirus, human metapneumovirus; viruses such as the picornaviridae, including: Human enterovirus A,B,C,D, Human rhinovirus A,B,C, Encephalomyocarditis virus, Theilovirus, Foot and mouth virus, Equine rhinitis A virus, Bovine Rhinitis B virus, Hepatitis A virus, Human Parechovirus, Ljungan virus, Aichi virus, Teschovirus, Sapeloviris, Senecavirus, Tremovirus, Aviheptovirus; viruses such as the rotoviridae, including: rotavirus A,B,C,D,E; viruses such as the papovaviridae.

It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

REFERENCES

1. Abbas, Z., W. Jafri, et al. "Hepatitis D: Scenario in the Asia-Pacific region." *World J Gastroenterol* 16(5): 554-62.

2. Ahima, R. S., H. R. Patel, et al. (2002). "Appetite suppression and weight reduction by a centrally active aminosterol." *Diabetes* 51(7): 2099-104.

3. Akhter, S., S. K. Nath, et al. (1999). "Squalamine, a novel cationic steroid, specifically inhibits the brush-border Na+/H+ exchanger isoform NHE3." *Am Physiol* 276(1 Pt 1): C136-44.

4. Alnouti, Y., J. S. Petrick, et al. (2006). "Tissue distribution and ontogeny of organic cation transporters in mice." *Drug Metab Dispos* 34(3): 477-82.

5. Arrigo, N. C., D. M. Watts, et al. (2008). "Experimental infection of *Aedes sollicitans* and *Aedes taeniorhynchus* with two chimeric Sindbis/Eastern equine encephalitis virus vaccine candidates." *Am J Trop Med Hyg* 78(1): 93-7.

6. Balasubramanian, A., N. Munshi, et al. (2005). "Structural proteins of Hepatitis C virus induce interleukin 8 production and apoptosis in human endothelial cells." *J Gen Virol* 86(Pt 12): 3291-301.

7. Bashirova, A. A., T. B. Geijtenbeek, et al. (2001). "A dendritic cell-specific intercellular adhesion molecule 3-grabbing nonintegrin (DC-SIGN)-related protein is highly expressed on human liver sinusoidal endothelial cells and promotes HIV-1 infection." *J Exp Med* 193(6): 671-8.

8. Bhargava, P., J. L. Marshall, et al. (2001). "A phase I and pharmacokinetic study of squalamine, a novel antiangiogenic agent, in patients with advanced cancers." *Clin Cancer Res* 7(12): 3912-9.

9. Breiner, K. M., H. Schaller, et al. (2001). "Endothelial cell-mediated uptake of a hepatitis B virus: a new concept of liver targeting of hepatotropic microorganisms." *Hepatology* 34(4 Pt 1): 803-8.

10. Bultmann, B. D., K. Klingel, et al. (2003). "Parvovirus B19: a pathogen responsible for more than hematologic disorders." *Virchows Arch* 442(1): 8-17.

11. Cardin, R. D., F. J. Bravo, et al. (2009). "Amphipathic DNA polymers exhibit antiviral activity against systemic murine Cytomegalovirus infection." *Virol J* 6: 214.

12. Carlson, J. R., W. L. Chang, et al. (2005). "Rhesus brain microvascular endothelial cells are permissive for rhesus cytomegalovirus infection." *J Gen Virol* 86(Pt 3): 545-9.

13. Coil, D. A. and A. D. Miller (2004). "Phosphatidylserine is not the cell surface receptor for vesicular stomatitis virus." *J Virol* 78(20): 10920-6.

14. Coil, D. A. and A. D. Miller (2005). "Enhancement of enveloped virus entry by phosphatidylserine." *J Virol* 79(17): 11496-500.

15. Coil, D. A. and A. D. Miller (2005). "Phosphatidylserine treatment relieves the block to retrovirus infection of cells expressing glycosylated virus receptors." *Retrovirology* 2: 49.

16. Erhardt, A., T. Gobel, et al. (2009). "Response to antiviral treatment in patients infected with hepatitis B virus genotypes E-H." *J Med Virol* 81(10): 1716-20.

17. Feldmann, A., M. K. Schafer, et al. (2000). "Targeted infection of endothelial cells by avian influenza virus A/FPV/Rostock/34 (H7N1) in chicken embryos." *J Virol* 74(17): 8018-27.

18. Finkielstein, C. V., M. Overduin, et al. (2006). "Cell migration and signaling specificity is determined by the phosphatidylserine recognition motif of Rac1." *J Biol Chem* 281(37): 27317-26.

19. Geimonen, E., S. Neff, et al. (2002). "Pathogenic and nonpathogenic hantaviruses differentially regulate endothelial cell responses." *Proc Natl Acad Sci USA* 99(21): 13837-42.

20. Genaidy, M., A. A. Kazi, et al. (2002). "Effect of squalamine on iris neovascularization in monkeys." *Retina* 22(6): 772-8.

21. Hao, D., L. A. Hammond, et al. (2003). "A Phase I and pharmacokinetic study of squalamine, an aminosterol angiogenesis inhibitor." *Clin Cancer Res* 9(7): 2465-71.

22. Harmon, B., N. Campbell, et al. "Role of Abl kinase and the Wave2 signaling complex in HIV-1 entry at a post-hemifusion step." *PLoS Pathog* 6(6): e1000956.

23. Hayer-Zillgen, M., M. Bruss, et al. (2002). "Expression and pharmacological profile of the human organic cation transporters hOCT1, hOCT2 and hOCT3." *Br J Pharmacol* 136(6): 829-36.

24. Hensley, L. E. and T. W. Geisbert (2005). "The contribution of the endothelium to the development of coagulation disorders that characterize Ebola hemorrhagic fever in primates." *Thromb Haemost* 94(2): 254-61.

25. Herbst, R. S., L. A. Hammond, et al. (2003). "A phase I/IIA trial of continuous five-day infusion of squalamine lactate (MSI-1256F) plus carboplatin and paclitaxel in patients with advanced non-small cell lung cancer." *Clin Cancer Res* 9(11): 4108-15.

26. Higgins, R. D., R. J. Sanders, et al. (2000). "Squalamine improves retinal neovascularization." *Invest Ophthalmol V is Sci* 41(6): 1507-12.

27. Higgins, R. D., Y. Yan, et al. (2004). "Regression of retinopathy by squalamine in a mouse model." *Pediatr Res* 56(1): 144-9.

28. Jessie, K., M. Y. Fong, et al. (2004). "Localization of dengue virus in naturally infected human tissues, by immunohistochemistry and in situ hybridization." *Infect Dis* 189(8): 1411-8.

29. Kelly, K. (2005). "The RGK family: a regulatory tail of small GTP-binding proteins." *Trends Cell Biol* 15(12): 640-3.

30. Kern, E. R. (2006). "Pivotal role of animal models in the development of new therapies for cytomegalovirus infections." *Antiviral Res* 71(2-3): 164-71.

31. Khaiboullina, S. F., A. A. Rizvanov, et al. (2005). "Yellow fever virus strains Asibi and 17D-204 infect human umbilical cord endothelial cells and induce novel changes in gene expression." *Virology* 342(2): 167-76.

32. Klenk, H. D. (2005). "Infection of the endothelium by influenza viruses." *Thromb Haemost* 94(2): 262-5.

33. Koepsell, H. (2004). "Polyspecific organic cation transporters: their functions and interactions with drugs." *Trends Pharmacol Sci* 25(7): 375-81.

34. Koepsell, H. and H. Endou (2004). "The SLC22 drug transporter family." *Pflugers Arch* 447(5): 666-76.

35. Kuge, O., Y. Akamatsu, et al. (1989). "Abortive infection with Sindbis virus of a Chinese hamster ovary cell mutant defective in phosphatidylserine and phosphatidylethanolamine biosynthesis." *Biochim Biophys Acta* 986(1): 61-9.

36. Leyssen, P., E. De Clercq, et al. (2000). "Perspectives for the treatment of infections with Flaviviridae." *Clin Microbiol Rev* 13(1): 67-82, table of contents.

37. Li, D., J. I. Williams, et al. (2002). "Squalamine and cisplatin block angiogenesis and growth of human ovarian cancer cells with or without HER-2 gene overexpression." *Oncogene* 21(18): 2805-14.

38. Lips, K. S., C. Volk, et al. (2005). "Polyspecific cation transporters mediate luminal release of acetylcholine from bronchial epithelium." *Am J Respir Cell Mol Biol* 33(1): 79-88.

39. Liu, L., Z. Xu, et al. (2005). "Vaccinia virus induces strong immunoregulatory cytokine production in healthy human epidermal keratinocytes: a novel strategy for immune evasion." *J Virol* 79(12): 7363-70.

40. Luplertlop, N. and D. Misse (2008). "MMP cellular responses to dengue virus infection-induced vascular leakage." *Jpn J Infect Dis* 61(4): 298-301.

41. MacDonald, D. (1995). "Squalamine for STDs." Abstract no F7 35th ICAAC conference.

42. McLaughlin, S. and D. Murray (2005). "Plasma membrane phosphoinositide organization by protein electrostatics." *Nature* 438(7068): 605-11.

43. Mercer, J. and A. Helenius (2008). "Vaccinia virus uses macropinocytosis and apoptotic mimicry to enter host cells." *Science* 320(5875): 531-5.

44. Minuesa, G., S. Purcet, et al. (2008). "Expression and functionality of anti-human immunodeficiency virus and anticancer drug uptake transporters in immune cells." *J Pharmacol Exp Ther* 324(2): 558-67.

45. Moore, K. S., S. Wehrli, et al. (1993). "Squalamine: an aminosterol antibiotic from the shark." *Proc Natl Acad Sci USA* 90(4): 1354-8.

46. Morrison, C., T. Gilson, et al. (2001). "Histologic distribution of fatal rotaviral infection: an immunohistochemical and reverse transcriptase in situ polymerase chain reaction analysis." *Hum Pathol* 32(2): 216-21.

47. Nikkels, A. F., S. Debrus, et al. (1995). "Localization of varicella-zoster virus nucleic acids and proteins in human skin." *Neurology* 45(12 Suppl 8): S47-9.

48. Noe, A., J. Plum, et al. (2005). "The latent HIV-1 reservoir in patients undergoing HAART: an archive of pre-HAART drug resistance." *J Antimicrob Chemother* 55(4): 410-2.

49. Pelkmans, L., E. Fava, et al. (2005). "Genome-wide analysis of human kinases in clathrin- and caveolae/raft-mediated endocytosis." *Nature* 436(7047): 78-86.

50. Pelkmans, L. and A. Helenius (2003). "Insider information: what viruses tell us about endocytosis." *Curr Opin Cell Biol* 15(4): 414-22.

51. Rao, M. N., A. E. Shinnar, et al. (2000). "Aminosterols from the dogfish shark *Squalus acanthias*." J Nat Prod 63(5): 631-5.

52. Reitman, M. L. and E. E. Schadt (2007). "Pharmacogenetics of metformin response: a step in the path toward personalized medicine." J Clin Invest 117(5): 1226-9.

53. Rong, Q., J. Huang, et al. (2007). "Infection of hepatitis B virus in extrahepatic endothelial tissues mediated by endothelial progenitor cells." Virol J 4: 36.

54. Ruiz, J. C., J. R. Beadle, et al. (2007). "Synthesis and antiviral evaluation of alkoxyalkyl-phosphate conjugates of cidofovir and adefovir." *Antiviral Res* 75(1): 87-90.

55. Salmi, C., C. Loncle, et al. (2008). "New stereoselective titanium reductive amination synthesis of 3-amino and polyaminosterol derivatives possessing antimicrobial activities." Eur J Med Chem 43(3): 540-7.

56. Salmi, C., C. Loncle, et al. (2008). "Squalamine: an appropriate strategy against the emergence of multidrug resistant gram-negative bacteria?" PLoS ONE 3(7): e2765.

57. Sbrana, E., S. Y. Xiao, et al. (2004). "Efficacy of post-exposure treatment of yellow fever with ribavirin in a hamster model of the disease." Am J Trop Med Hyg 71(3): 306-12.

58. Schiller, J. H. and G. Bittner (1999). "Potentiation of platinum antitumor effects in human lung tumor xenografts by the angiogenesis inhibitor squalamine: effects on tumor neovascularization." Clin Cancer Res 5(12): 4287-94.

59. Selinsky, B. S., R. Smith, et al. (2000). "Squalamine is not a proton ionophore." Biochim Biophys Acta 1464(1): 135-41.

60. Selinsky, B. S., Z. Zhou, et al. (1998). "The aminosterol antibiotic squalamine permeabilizes large unilamellar phospholipid vesicles." Biochim Biophys Acta 1370(2): 218-34.

61. Sills, A. K., Jr., J. I. Williams, et al. (1998). "Squalamine inhibits angiogenesis and solid tumor growth in vivo and perturbs embryonic vasculature." Cancer Res 58(13): 2784-92.

62. Slitt, A. L., N. J. Chemington, et al. (2002). "Tissue distribution and renal developmental changes in rat organic cation transporter mRNA levels." Drug Metab Dispos 30(2): 212-9.

63. Sokoloff, M. H., C. W. Rinker-Schaeffer, et al. (2004). "Adjunctive therapy for men with high risk localized and locally advanced prostate cancer: targeting disseminated tumor cells." J Urol 172(6 Pt 2): 2539-44.

64. Steinberg, B. E. and S. Grinstein (2008). "Pathogen destruction versus intracellular survival: the role of lipids as phagosomal fate determinants." J Clin Invest 118(6): 2002-11.

65. Sumikoshi, M., K. Hashimoto, et al. (2008). "Human influenza virus infection and apoptosis induction in human vascular endothelial cells." J Med Virol 80(6): 1072-8.

66. Sung, J. H., K. H. Yu, et al. (2005). "Saturable distribution of tacrine into the striatal extracellular fluid of the rat: evidence of involvement of multiple organic cation transporters in the transport." Drug Metab Dispos 33(3): 440-8.

67. Tesh, R. B., H. Guzman, et al. (2001). "Experimental yellow fever virus infection in the Golden Hamster (*Mesocricetus auratus*). I. Virologic, biochemical, and immunologic studies." J Infect Dis 183(10): 1431-6.

68. US2005/0261508A1 (2005). "Aminosterol Compounds useful as inhibitors of the sodium/proton exchanger (NHE), pharmaceutical methods, and compositions employing such inhibitors, and processes for evaluating the NHE-inhibitory efficacy of compounds," Zasloff et al., Published Nov. 24, 2005.

69. US2006/0166950A1 (2006). "Treatment of neovascularization disorders with squalamine," Zasloff et al., Published Jun. 27, 2006

70. US2006/0183928A1 (2006). "Aminosterol Compounds useful as inhibitors of the sodium/proton exchanger (NHE), pharmaceutical methods, and compositions employing such inhibitors, and processes for evaluating the NHE-inhibitory efficacy of compounds", Published Aug. 17, 2006

71. US2007/10504A1 (2007). "Polymorphic and Amorphous salt forms of squalamine dilactate" Chellquist, Doubleday, Gilbert, Zhang, McLane, Armbruster, Levitt, Published Jan. 11, 2007

72. U.S. Pat. No. 5,192,756 (1993). "Aminosterol antibiotic," Zasloff, Moore, Wehrli. Issued Mar. 9, 1993

73. U.S. Pat. No. 5,637,691 (1993). "Steroid derivatives, pharmaceutical compositions containing them, and their use as antibiotics and disinfectants", Frye, Zasloff, Kinney, Moriarty.

74. U.S. Pat. No. 5,721,226 (1998). Methods for treating angiogenesis using squalamine and squalamine steroid derivatives Frye, Zasloff, Kinney, Moriarty, Collins 75. U.S. Pat. No. 5,733,899 (1998). Methods for treating infections using steroid based pharmaceutical compositions. Frye, Zasloff, Kinney, Moriarty, Collins 76. U.S. Pat. No. 5,763,430 (1998). "Method of treating a viral infection by administering a steroid compound" Zasloff.

77. U.S. Pat. No. 5,792,635 (1998). "Method of inhibiting the sodium-proton exchanger NHE3 and method of inhibiting growth by administering squalamine," Zasloff.

78. U.S. Pat. No. 5,795,885 (1998). Method of Inhibiting proliferation of cells by administering an aminosterol compound Zasloff, Shinnar, Kinney, Anderson, Williams, McLane.

79. U.S. Pat. No. 5,834,453 (1998). "Methods for the manufacture and use of antimicrobial sterol conjugates" Regen (Leheigh Univ).

80. U.S. Pat. No. 5,840,740 (1998). "Aminosterol compounds and a method of treating infection using the aminosterol compounds" Zasloff, Shinnar, Kinney, Rao.

81. U.S. Pat. No. 5,840,936 (1998). "Aminosterol compounds useful as inhibitors of the sodium/proton exchanger (NHE)" Zasloff, Shinnar, Rao, Kinney 82. U.S. Pat. No. 5,847,172 (1998). "Certain Aminosterol compounds and Pharmaceutical compositions including these compounds." Zasloff, Shinnar, Kinney, Jones.

83. U.S. Pat. No. 5,856,535 (1999). "Aminosterol ester compounds" Zasloff, Kinney, Jones.

84. U.S. Pat. No. 5,874,597 (1999). "Certain Aminosterol compounds and pharmaceutical compositions including these compounds," Jones, Issued Feb. 23, 1999.

85. U.S. Pat. No. 5,994,336 (1999). "Method of inhibiting proliferation of cells by administering an aminosterol compound" Zasloff, Shinnar, Kinney, Rao, Issued Nov. 30, 1999.

86. U.S. Pat. No. 6,017,906 (2000). "Polyamine conjugates for treatment of infection" Mintz, C S et al Intercardia, Inc., Issued Jan. 25, 2000

87. U.S. Pat. No. 6,143,738 (2000). "Therapeutic uses for an aminosterol compound." Zasloff, Issued Nov. 7, 2000

88. U.S. Pat. No. 6,147,060 (2000). "Treatment of carcinomas using squalamine in combination with other anticancer agents" Zasloff, Williams, Issued Nov. 14, 2000

89. U.S. Pat. No. 6,388,108B1 (2002). "Aminosterol compounds and uses thereof" Rao, Feibush, Kinney, Zasloff, Noecker, Issued May 14, 2002.

90. U.S. Pat. No. 6,596,712B2 (2003). "Treatment of carcinomas using squalamine in combination with other anticancer agents or modalities" Zasloff, Williams, Sokoloff, Issued Jul. 22, 2003.

91. U.S. Pat. No. 6,962,909B2 (2005). "Treatment of neovascularization disorders with squalamine", Zasloff, Shinnar, Kinney, Jones, Issued Nov. 8, 2005.

92. Verdin, E. M., G. L. King, et al. (1989). "Characterization of a common high-affinity receptor for reovirus serotypes 1 and 3 on endothelial cells." J Virol 63(3): 1318-25.

93. Wang, E., O. Petrakova, et al. (2007). "Chimeric Sindbis/eastern equine encephalitis vaccine candidates are highly attenuated and immunogenic in mice." *Vaccine* 25(43): 7573-81.

94. Williams, J. I., S. Weitman, et al. (2001). "Squalamine treatment of human tumors in nu/nu mice enhances platinum-based chemotherapies." Clin Cancer Res 7(3): 724-33.

95. WO96/08270 (1996). "Method for inhibiting sexually transmitted diseases using Magainin antimicrobials or Squalamine Compounds" Jacob, Zasloff, Williams, Bedi.

96. Wong, K. T., W. J. Shieh, et al. (2002). "Nipah virus infection: pathology and pathogenesis of an emerging paramyxoviral zoonosis." Am J Pathol 161(6): 2153-67.

97. Xiao, S. Y., H. Zhang, et al. (2001). "Experimental yellow fever virus infection in the Golden hamster (*Mesocricetus auratus*). II. Pathology." J Infect Dis 183(10): 1437-44.

98. Yao, L., C. Korteweg, et al. (2008). "Avian influenza receptor expression in H5N1-infected and noninfected human tissues." Faseb J 22(3): 733-40.

99. Yeung, T., G. E. Gilbert, et al. (2008). "Membrane phosphatidylserine regulates surface charge and protein localization." Science 319(5860): 210-3.

100. Yeung, T., M. Terebiznik, et al. (2006). "Receptor activation alters inner surface potential during phagocytosis." Science 313(5785): 347-51.

101. Yin, M., C. Gentili, et al. (2002). "Antiangiogenic treatment delays chondrocyte maturation and bone formation during limb skeletogenesis." J Bone Miner Res 17(1): 56-65.

102. Zamudio-Meza, H., A. Castillo-Alvarez, et al. (2009). "Cross-talk between Rac1 and Cdc42 GTPases regulates formation of filopodia required for dengue virus type-2 entry into HMEC-1 cells." *J Gen Virol* 90(Pt 12): 2902-11.

103. Zasloff, M. (2002). "Antimicrobial peptides of multicellular organisms." Nature 415(6870): 389-95.

104. Zasloff, M., J. I. Williams, et al. (2001). "A spermine-coupled cholesterol metabolite from the shark with potent appetite suppressant and antidiabetic properties." Int J Obes Relat Metab Disord 25(5): 689-97.

105. Arrigo, N. C., D. M. Watts, et al. (2008). "Experimental infection of *Aedes sollicitans* and *Aedes taeniorhynchus* with two chimeric Sindbis/Eastern equine encephalitis virus vaccine candidates." *Am J Trop Med Hyg* 78(1): 93-7.

106. Cardin, R. D., F. J. Bravo, et al. (2009). "Amphipathic DNA polymers exhibit antiviral activity against systemic murine Cytomegalovirus infection." *Virol J* 6: 214.

107. Cavanaugh, V. J., Y. Deng, et al. (2003). "Vigorous innate and virus-specific cytotoxic T-lymphocyte responses to murine cytomegalovirus in the submaxillary salivary gland." *J Virol* 77(3): 1703-17.

108. Erhardt, A., T. Gobel, et al. (2009). "Response to antiviral treatment in patients infected with hepatitis B virus genotypes E-H." *J Med Virol* 81(10): 1716-20.

109. Harmon, B., N. Campbell, et al. "Role of Abl kinase and the Wave2 signaling complex in HIV-1 entry at a post-hemifusion step." *PLoS Pathog* 6(6): e1000956.

110. Jessie, K., M. Y. Fong, et al. (2004). "Localization of dengue virus in naturally infected human tissues, by immunohistochemistry and in situ hybridization." *J Infect Dis* 189(8): 1411-8.

111. Kern, E. R. (2006). "Pivotal role of animal models in the development of new therapies for cytomegalovirus infections." *Antiviral Res* 71(2-3): 164-71.

112. Noe, A., J. Plum, et al. (2005). "The latent HIV-1 reservoir in patients undergoing HAART: an archive of pre-HAART drug resistance." *J Antimicrob Chemother* 55(4): 410-2.

113. Paessler, S., P. Aguilar, et al. (2004). "The hamster as an animal model for eastern equine encephalitis—and its use in studies of virus entrance into the brain." *J Infect Dis* 189(11): 2072-6.

114. Ruiz, J. C., J. R. Beadle, et al. (2007). "Synthesis and antiviral evaluation of alkoxyalkyl-phosphate conjugates of cidofovir and adefovir." *Antiviral Res* 75(1): 87-90.

115. Wang, E., O. Petrakova, et al. (2007). "Chimeric Sindbis/eastern equine encephalitis vaccine candidates are highly attenuated and immunogenic in mice." *Vaccine* 25(43): 7573-81.

116. Zamudio-Meza, H., A. Castillo-Alvarez, et al. (2009). "Cross-talk between Rac1 and Cdc42 GTPases regulates formation of filopodia required for dengue virus type-2 entry into HMEC-1 cells." *J Gen Virol* 90(Pt 12): 2902-11.

What is claimed:

1. An in vivo method of treating a viral infection in a mammal comprising administering a composition comprising:
    (a) a pharmaceutically acceptable grade of squalamine or a pharmaceutically acceptable salt thereof in an amount sufficient to produce an antiviral effect, and
    (b) at least one pharmaceutically acceptable carrier,
    wherein the viral infection is caused by a virus selected from the group consisting of Cytomegalovirus, Herpes Simplex virus, Herpes Zoster virus, Orthomyxoviridae, and Picornaviridae, and
    wherein the composition is systemically administered intravenously, subcutaneously, intramuscularly, orally, or by inhalation.

2. The method of claim 1, wherein the amount is an effective daily dosing amount of about 0.1 to 20 mg/kg body weight.

3. The method of claim 1, wherein the composition is administered in a regimen that achieves and maintains a tissue concentration of squalamine in body organs and tissues of between about 0.1-200 µg/gram (tissue wet weight).

4. The method of claim 1, wherein the mammal is human.

5. The method of claim 1, wherein:
    (a) the composition does not demonstrate an altered $IC_{50}$ or $IC_{90}$ (drug concentration required to inhibit viral growth by 50% or 90% respectively) over time;

(b) the composition demonstrates an $IC_{50}$ or $IC_{90}$ which does not increase by more than 0%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, or 30% over time;

(c) the composition demonstrates an $IC_{50}$ or $IC_{90}$ which does not increase by an amount described in (b) over a time period selected from the group consisting of 1 week, 2 weeks, 3 weeks, 4 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1 year, 1.5 years, 2 years, 2.5 years, 3 years, 3.5 years, 4 years, 4.5 years, and 5 years; or (d) any combination thereof.

6. The method of claim 1, wherein the Orthomyxoviridae is selected from the group consisting of Influenza A, Influenza B, and parainfluenza.

7. The method of claim 1, wherein the Picomaviridae is selected from the group consisting of Rhinovirus and Poliovirus.

8. The method of claim 1, wherein the method further comprises administration of an adjuvant.

9. The method of claim 8, wherein the adjuvant is selected from the group consisting of cytokines and/or interleukins alum, Lipid A, including monophosphoryl lipid A, bacterial products, endotoxins, cholesterol, fatty acids, aliphatic amines, paraffinic and vegetable oils, threonyl derivative, and muramyl dipeptide, alum, alum plus deoxycholate (ImmunoAg), MTP-PE (Biocine Corp.), QS21 (Genentech, Inc.), BCG, MPL, nonviable preparations of Corynebacterium, parvum, Monophosphoryl lipid immunomodulator, AdjuVax 100a, QS-21, QS-18, CRL1005, Aluminum salts, MF-59, and Virosomal adjuvant technology.

10. The method of claim 1, wherein the composition further comprises at least one antigen capable of eliciting an immune response.

11. The method of claim 10, wherein the antigen is selected from the group consisting of viral and prion antigens.

12. The method of claim 9, wherein the cytokine and/or interleukin is selected from the group consisting of IL2, IL3, IL4, ILS, IL6, IL7, IL8, IL-9, IL10, IL-11, IL12, IL13, IL-14, IL15, IIL16, IL-17, IL-18, IL-19, IL-20, IL-21, anti-CD40, CD40 L, IFN-gamma, TNF-alpha, IL-Ialpha, IL-lbeta.

13. The method of claim 1, wherein the virus is Cytomegalovirus.

14. The method of claim 1, wherein the virus is Herpes Simplex virus.

15. The method of claim 1, wherein the virus is Herpes Zoster virus.

16. The method of claim 1, wherein the virus is Orthomyxoviridae.

17. The method of claim 1, wherein the virus is Picomaviridae.

18. The method of claim 1, wherein the composition is administered orally.

19. The method of claim 1, wherein the composition is administered intravenously, subcutaneously, or intramuscularly.

20. The method of claim 1, wherein the composition is administered by inhalation.

* * * * *